United States Patent
Shiina et al.

(10) Patent No.: US 8,115,008 B2
(45) Date of Patent: Feb. 14, 2012

(54) METHOD FOR PRODUCING OPTICALLY ACTIVE ESTER AND METHOD FOR PRODUCING OPTICALLY ACTIVE CARBOXYLIC ACID

(75) Inventors: Isamu Shiina, Tokyo (JP); Kenya Nakata, Tokyo (JP)

(73) Assignee: Tokyo University of Science Education Foundation Administrative Organization, Tokyo (JP)

( * ) Notice: Subject to any disclaimer, the term of this patent is extended or adjusted under 35 U.S.C. 154(b) by 0 days.

(21) Appl. No.: 12/675,326

(22) PCT Filed: Mar. 4, 2009

(86) PCT No.: PCT/JP2009/054012
§ 371 (c)(1),
(2), (4) Date: Feb. 25, 2010

(87) PCT Pub. No.: WO2009/113428
PCT Pub. Date: Sep. 17, 2009

(65) Prior Publication Data
US 2010/0234610 A1    Sep. 16, 2010

(30) Foreign Application Priority Data

Mar. 11, 2008 (JP) ................. 2008-061512
Mar. 28, 2008 (JP) ................. 2008-087223
Oct. 7, 2008 (JP) ................. 2008-260902

(51) Int. Cl.
C07C 69/76 (2006.01)
C07C 67/00 (2006.01)
C07D 513/14 (2006.01)
(52) U.S. Cl. .................. 548/151; 560/100; 560/101
(58) Field of Classification Search .......... None
See application file for complete search history.

(56) References Cited

FOREIGN PATENT DOCUMENTS

EP       0021806 A1 * 1/1981
JP       9-143101      6/1997
WO       WO 2008/140074  11/2008

OTHER PUBLICATIONS

Shiina et al. Eur. J. Org. Chem.—Short Communications (2008), 35, pp. 5887-5890.*
"Benzotetramisole: A Remarkably Enantioselective Acyl Transfer Catalyst", Birman et al., Organic Letters, 2006 vol. 8, No. 7 pp. 1351-1354.
"Kinetic Resolution of Propargylic Alochols Catalyzed by Benzotetramisole," Birman et al., Organic Letters, 2006, vol. 8, No. 21 pp. 4859-4861.
"The first asymmetric esterification of free carboxylic acids with racemic alcohols using benzoic anhydrides and tetramisole derivatives: an application to the kinetic resolution of secondary benzylic alcohols," Shiina et al., Tetrahedron letters, 2007, vol. 48, pp. 8314-8317.
"Kinetic Optical Resolution of Various Racemic Secondary Benzyl Alcohols Using a Substituted Benzoic Anhydride Method," Tanaka et al., The 94th Symposium on Organic Synthesis, Japan, Oct. 30, 2008, pp. 14-15.
"Kinetic Optical Resolution of Racemic Carboxylic Acids and Alcohols with Substituted Benzoic Anhydride as Dehydrating Agent," Tanaka et al., The 93rd Symposium on Organic Synthesis, Japan, May 30, 2008, pp. 1-4.

* cited by examiner

Primary Examiner — Kamal Saeed
Assistant Examiner — Nyeemah A Grazier
(74) Attorney, Agent, or Firm — Day Pitney LLP

(57) ABSTRACT

Disclosed is a method for producing an optically active ester by highly selectively esterifying one enantiomer of a racemic carboxylic acid, while producing an optically active carboxylic acid which is the other enantiomer. An optically active ester is produced while producing an optically active carboxylic acid at the same time by reacting a racemic carboxylic acid with a specific alcohol or phenol derivative in the presence of benzoic anhydride or a derivative thereof and a catalyst such as tetramisole or benzotetramisole, thereby selectively esterifying one enantiomer of the racemic carboxylic acid.

1 Claim, No Drawings

METHOD FOR PRODUCING OPTICALLY ACTIVE ESTER AND METHOD FOR PRODUCING OPTICALLY ACTIVE CARBOXYLIC ACID

This application is a 371 of International Application No.: PCT/JP2009/054012 filed Mar. 4, 2009, which in turn claims priority from Japanese Application Nos.: 2008-061512, 2008-087223 and 2008-260902, all of which are incorporated herein by reference.

TECHNICAL FIELD

The present invention relates to a method for producing an optically active ester and a method for producing an optically active carboxylic acid, and more specifically, it relates to a method for producing an optically active ester where one enantiomer of a racemic carboxylic acid is selectively esterified, and in addition, it relates to a method for producing an optically active carboxylic acid which is the other enantiomer.

BACKGROUND ART

Optically active esters and optically active carboxylic acids are used in various fields such as pharmaceutical products, intermediates of biologically active substances, intermediates of natural product synthesis, and the like.

In the background art, as a method for producing an optically active ester, a method of production from a racemic secondary benzyl alcohol in the presence of an acid anhydride, using tetramisole or benzotetramisole as a catalyst has been known (see Non-Patent Document 1). Further, a method for producing an optically active ester from a racemic propargylic alcohol in the presence of an acid anhydride using benzotetramisole as a catalyst has been known (see Non-Patent Document 2). However, these production methods have the problem that the structures of the acid anhydride are very limited, and the like, and the substrate generality is poor. Thus, the present inventors have previously proposed a method for producing an optically active ester by reacting a racemic secondary benzyl alcohol and a free carboxylic acid in the presence of a benzoic anhydride or its derivative, using tetramisole or benzotetramisole as a catalyst (see Non-Patent Document 3).

On the other hand, as a method for producing an optically active carboxylic acid, a method of crystallization separation of a diastereomer salt of a racemic carboxylic acid and a separation agent, using an optically active amine as a separation agent has been known (see Patent Document 1). However, this production method has the problems of high substrate specificity, and that the identification of an optically active amine suitable for the structure of the carboxylic acid, and the selection of the recrystallization solvent are difficult. Further, because the separation is repeated multiple times, the operation is complicated.

Non-Patent Document 1: Birman, V. B.; Li, X.; Org. Lett.; 2006, 7, pp. 1351-1354
Non-Patent Document 2: Birman, V. B.; Guo, L.; Org. Lett.; 2006, 21, pp. 4859-4861
Non-Patent Document 3: Shiina, I.; Nakata, K.; Tetrahedron Lett.; 2007, 48, pp. 8314-8317
Patent Document 1: Japanese Unexamined Patent Publication No. H9-143101

DISCLOSURE OF THE INVENTION

Problems to be Solved by the Invention

Incidentally, in the above described production methods of an optically active ester, because one of the enantiomers of the racemic alcohol is selectively esterified to become an optically active ester, the other enantiomer remains as an optically active alcohol. Accordingly, if a racemic carboxylic acid and an alcohol were reacted, and one of the enantiomers of the racemic carboxylic acid could be selectively esterified, it could be considered possible to produce an optically active carboxylic acid along with the production of an optically active ester, but such a method of production has not been carried out in the prior art.

The present invention, in consideration of the above problems, has the objective of providing a method for producing an optically active ester by highly selective esterification of one of the enantiomers of a racemic carboxylic acid, along with providing a method for producing an optically active carboxylic acid which is the other enantiomer.

Means for Solving the Problems

The present inventors carried out diligent research to solve the above problem. As a result, they achieved the completion of the present invention by discovering that the above problem can be solved by reacting a racemic carboxylic acid and a specified alcohol or phenol derivative under specified conditions. More specifically, the present invention is as follows.

The first aspect of the present invention is a method for producing an optically active ester comprising reacting a racemic carboxylic acid and an alcohol shown by the formula (a) below or a phenol derivative shown by the formula (b) below, in the presence of a benzoic anhydride or its derivative and a catalyst shown by any of the formulae (c) to (f) below, and selectively esterifying one enantiomer of the racemic carboxylic acid

(in the formula (a), $R^a$ represents a phenyl group, naphthyl group, anthryl group, or phenanthryl group, which may have a substituent group);

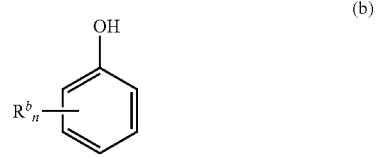

(in the formula (b), $R^b$ represents a phenyl group, naphthyl group, anthryl group, or phenanthryl group, which may have a substituent group; n represents an integer of 1 to 5; and in the case that a plurality of $R^b$ is present, they may be the same or different);

(in the formulae (c) to (f), X represents any of the following substituent groups,

—CH₃   —CH(CH₃)₂   —CH₂—CH(CH₃)₂

—CH(CH₃)(CH₂—CH₃)   —CH₂—OR   —CH(CH₃)(OR)

—(CH₂)₂—S—CH₃   —CH₂—SR

—(CH₂)₄—NHR   —CH₂CONHR   —(CH₂)₂CONHR

—C₆H₅   —CH₂—C₆H₅

—CH₂—C₆H₄—OR

—CH₂-imidazole   —CH₂-indole and R represents a protecting group).

The racemic carboxylic acid may be shown by the formula (g) below (g)

(in the formula (g), $R^{g1}$ and $R^{g2}$ represent organic groups which differ from each other).

In the preferred embodiment, one of the carbon atoms of $R^{g1}$ and $R^{g2}$ bonded to the asymmetric carbon is bonded to another atom by a multiple bond.

In the formula (b), $R^b$ is preferably a naphthyl group, substituted at the 2,6 positions of the phenol.

The second aspect of the invention is a method for producing an optically active carboxylic acid comprising reacting a racemic carboxylic acid and an alcohol shown by the formula (a) below or a phenol derivative shown by the formula (b) below, in the presence of a benzoic anhydride or its derivative and a catalyst shown by one of formulae (c) to (f) below, and selectively esterifying one enantiomer of the racemic carboxylic acid (a)

(in the formula (a), $R^a$ represents a phenyl group, naphthyl group, anthryl group, or phenanthryl group, which may have a substituent group);

(b)

(in the formula (b), $R^b$ represents a phenyl group, naphthyl group, anthryl group, or phenanthryl group, which may have a substituent group; and n represents an integer of 1 to 5; and in the case that a plurality of $R^b$ is present, they may be the same or different);

(in the formulae (c) to (f), X represents any of the following substituent groups,

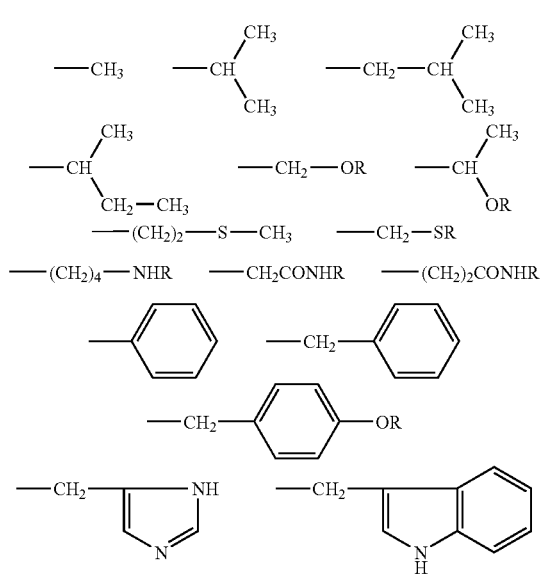

and R represents a protecting group).

EFFECTS OF THE INVENTION

According to the present invention, it is possible to produce an optically active ester by highly selective esterification of one of the enantiomers of a racemic carboxylic acid, along with the production of an optically active carboxylic acid of the other enantiomer.

PREFERRED MODE FOR CARRYING OUT THE INVENTION

The method for producing an optically active ester and the method for producing an optically active carboxylic acid of the present invention are characterized in reacting a racemic carboxylic acid and a specified alcohol or a phenol derivative, in the presence of a benzoic anhydride or its derivative, and a specified catalyst, and selectively esterifying one enantiomer of the racemic carboxylic acid.

The optically active ester and the optically active carboxylic acid obtained by the production method of the present invention respectively correspond to the different enantiomers of the racemic carboxylic acid. Accordingly, the method for producing the optically active ester and the method for producing the optically active carboxylic acid according to the present invention can be understood to be a method of optical resolution of a racemic carboxylic acid.

Racemic Carboxylic Acid

The racemic carboxylic acid used in the production method of the present invention is not particularly limited, but preferably has an asymmetric carbon at the a position of the carboxyl group as shown below in formula (g).

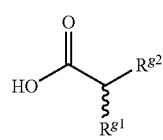

(g)

In the above formula (g), $R^{g1}$ and $R^{g2}$ represent organic groups which differ from each other. As the organic groups, alkyl group, alkenyl group, alkynyl group, aryl group, heteroaryl group, alkoxyalkyl group, alkoxyalkenyl group, alkoxyalkynyl group, arylalkyl group, arylalkenyl group, heteroarylalkyl group, heteroarylalkenyl group, heteroarylalkynyl group, alkylaryl group, alkylheteroaryl group, alkoxyaryl group, alkoxyheteroaryl group and the like can be mentioned. These organic groups may be optionally substituted by an alkyl group, alkoxy group, aryl group, heteroaryl group, acyl group, halogen atom and the like.

Further, for $R^{g1}$ and $R^{g2}$, it is preferable that one of the carbon atoms of $R^{g1}$ and $R^{g2}$ which bonds to the asymmetric carbon is bonded by a multiple bond to another atom, and that the other carbon atom is bonded by a single bond to another atom. In this way, it is possible to increase the enantiomer selectivity rate. Because the carbon atom bonded to the asymmetric carbon is bonded to another atom by a multiple bond, the asymmetric carbon may be bonded to an alkenyl group, alkynyl group, aryl group, heteroaryl group, or the like.

Alcohol

The alcohol used in the production method of the present invention is shown by formula (a) below.

(a)

In the above formula (a), $R^a$ represents a phenyl group, naphthyl group, anthryl group, or phenanthryl group which may have a substituent group. As the substituent group of $R^a$, an alkyl group, alkoxy group, aryl group, halogen atom and the like may be mentioned. In particular, as $R^a$, the 2-tolyl group, 1-naphthyl group, and 9-phenanthryl group are preferable. By using such an alcohol, it is possible to produce an optically active ester and optically active carboxylic acid with a high enantiomer selectivity rate.

Phenol Derivative

The phenol derivative used in the production method of the present invention is shown by the formula (b) below.

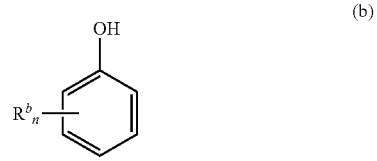

(b)

In the above formula (b), $R^b$ represents preferably a phenyl group, naphthyl group, anthryl group, or phenanthryl group, which may have a substituent group. As the substituent group of $R^b$, an alkyl group, alkoxy group, aryl group, halogen atom and the like can be mentioned. Further, n represents an integer of 1 to 5, and n=2 is preferable. In the case that a plurality of $R^b$ are present, they may be the same or different. Among these phenol derivatives, one where the 2,6 positions of the phenol are substituted with naphthyl groups is preferable.

Benzoic Anhydride or its Derivative

The benzoic anhydride or its derivative used in the production method of the present invention functions as a dehydrating condensing agent. As the derivative of the benzoic anhydride, one obtained from benzoic acid where an electrondonating group such as an alkyl group, alkoxy group, amino group, hydroxyl group or the like is bonded to the phenyl group is preferable, and one obtained from a 1 to 3 substituted benzoic acid group with alkyl groups or alkoxy groups of 1 to 3 carbons bonded thereto is more preferable.

Catalyst

The catalyst used in the production method of the present invention is shown by the below formulae (c) to (f).

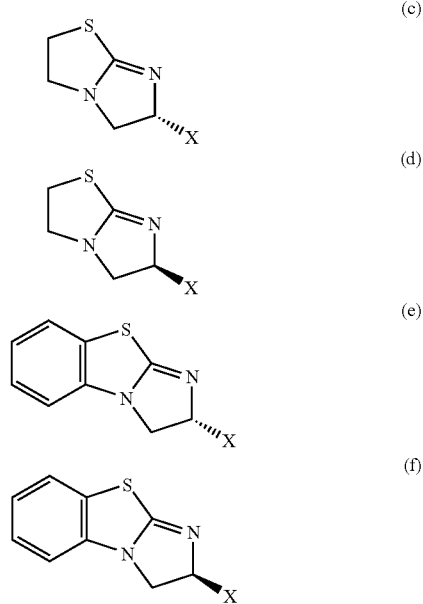

In the above formulae (c) to (f), X represents any of the substituent groups below. R represents a protecting group such as an alkyl group, acyl group, silyl group, or the like.

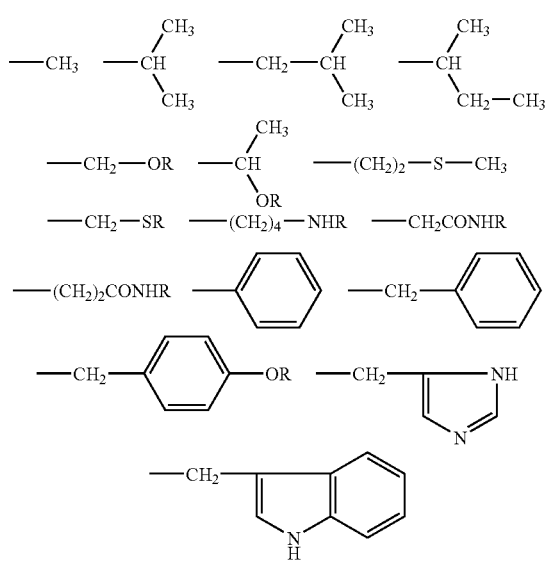

Among the catalysts shown by formulae (c) to (f) above, the catalyst shown by the above formula (d), when X is a phenyl group, is known as tetramisole, and the catalyst shown by the above formula (e), when X is a phenol group, is known as benzotetramisole. These catalysts are commercially available, and can also be synthesized using an amino acid as the side chain of the substituent group shown by X.

Reaction Conditions and the Like

The production of the optically active ester and the optically active carboxylic acid is carried out by adding a racemic carboxylic acid, an alcohol or a phenol derivative, a benzoic anhydride or its derivative, and the catalyst to the solvent. As the solvent, dichloromethane, chlorobenzene or the like can be mentioned. Further, in order to neutralize the acid originating from the benzoic anhydride or its derivative generated as the reaction progresses, it is preferable to add a base into the reaction system. As this base, an organic base not having nucleophilicity (trimethylamine, triethylamine, diisopropylethylamine) is preferable.

The sequence of addition into the solvent is arbitrary, but it is preferable to add the base, catalyst, and alcohol or phenol derivative in order to the solution containing the racemic carboxylic acid and the benzoic anhydride or its derivative.

The respective addition amounts are not particularly limited, but are preferably, with respect to the racemic carboxylic acid, 0.5 to 1.0 equivalents of the alcohol or phenol derivative, 0.5 to 1.5 equivalents of the benzoic anhydride or its derivative, 1.0 to 3.0 equivalents of the base, and 0.1 to 10 mol % of the catalyst.

The reaction temperature is preferably −23 to 30° C., and the reaction time is preferably 10 min to 48 hr.

EXAMPLES

Hereinafter, the present invention is explained more detail by way of Examples, but the scope of the present invention is not limited by these Examples.

Experimental Example 1

Production of Optically Active Ester and Optically Active Carboxylic Acid Using a Variety of Alcohols

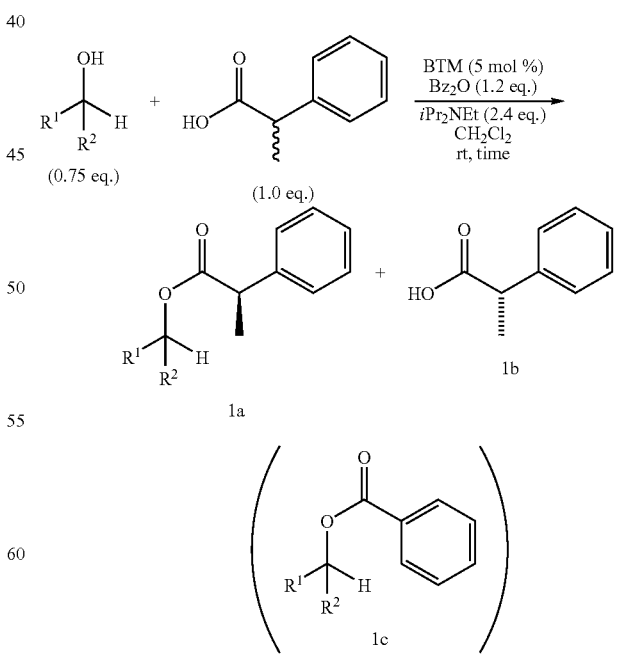

As shown in the above reaction equation, by adding at room temperature in order, 2.4 eq of diisopropylethylamine to a dichloromethane solution including 1.2 eq of benzoic anhydride ($Bz_2O$) and 1.0 eq racemic 2-phenylpropionic acid, and 5 mol % benzotetramisole (BTM) with respect to the carboxylic acid, and 0.75 eq of alcohol, after stirring the reaction mixture solution for a predetermined time at room temperature, the reaction was stopped with saturated ammonium chloride water. After fractionating the organic layer, the aqueous layer was extracted 3 or 4 times with diethylether or dichloromethane. After combining the organic layers, they were dried with anhydrous sodium sulfate. After filtering the solution, it was vacuum concentrated, and the obtained mixture was fractionated by thin layer silica gel chromatography to obtain the corresponding optically active ester and a part of the unreacted optically active carboxylic acid. Then 1 M hydrochloric acid was added to the water layer, and after adjusting the pH to 2, extraction was carried out 4 times with diethyl ether or dichloromethane. After-treatment was carried out in the same way as above, and unreacted optically active carboxylic acid was further recovered, and added to the previously obtained optically active carboxylic acid. The results are shown in Table 1.

The enantiomeric excess ratio ee was measured by the HPLC analysis method with a chiral column. Further, the reaction rate ratio s was calculated as s=[ln(1−C)(1−ee of product))]/[ln(1−C)(1+ee of product)], according to the method of Kagan (Top. Stereochem., 1988, 18, pp. 249-330).

TABLE 1

| No. | $R^1$ | $R^2$ | Time | Yield of 1a/% (1a/1c) | Yield of 1b/% | ee/% 1a/1b | s |
|---|---|---|---|---|---|---|---|
| 1 | Ph | H | 12 h | 40 (8/1) | 60 | 33/23 | 2 |
| 2 |  | c-Hex | 3 d | 39 (23/1) | 31 | 0/3 | 1 |
| 3 | Ph | Ph | 12 h | 42 (99/1) | 37 | 33/19 | 2 |
| 4 | 2-$MeC_6H_4$ | 2-$MeC_6H_4$ | 6 h | 32 (85/1) | 39 | 89/34 | 24 |
| 5 | Bn | Bn | 16 h | 12 (>99/1) | 5 | 3/0.03 | 1 |
| 6 | 1-Nap | 1-Nap | 4 h | 40 (46/1) | 6 | 82/52 | 17 |
| 7 | 2-Nap | 2-Nap | 11 h | 51 (>99/1) | 1 | 26/37 | 2 |
| 8 | 9-Phe | 9-Phe | 40 m | 31 (>99/1) | 33 | 84/28 | 15 |

As can be understood from Table 1, when using as an alcohol 1,1-di(2-tolyl)methanol, 1,1-diphenylmethanol, 1,1-di(1-naphthyl)methanol, 1,1-di(2-napthyl)methanol, or 1,1-di(9-phenanthryl)methanol (Entries 3, 4, and 6 to 8), in particular 1,1-di(2-tolyl)methanol, 1,1-di(1-naphthyl)methanol, or 1,1-di(9-phenanthryl)methanol, it is possible to obtain the optically active esters and optically active carboxylic acids with a higher enantiomeric selectivity rates than for the case of using other alcohols (Entries 1,2, and 5).

Experimental Example 2

Production of Optically Active Ester and Optically Active Carboxylic Acid Using Various Phenol Derivatives

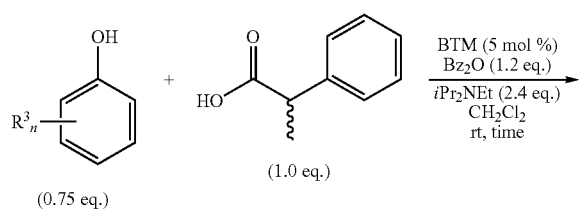

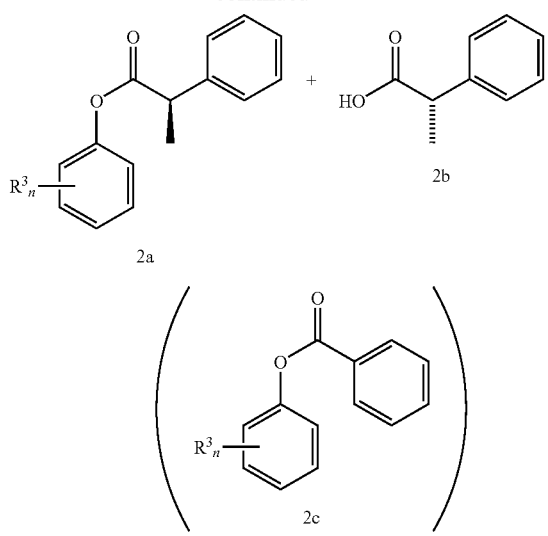

As shown in the above reaction equation, by adding at room temperature in order, 2.4 eq of diisopropylethylamine to a dichloromethane solution including 1.2 eq of benzoic anhydride ($Bz_2O$) and 1.0 eq racemic 2-phenylpropionic acid, and 5 mol % benzotetramisole (BTM) with respect to the carboxylic acid, and 0.75 eq of phenol derivative, after stirring the reaction mixture solution for a predetermined time at room temperature, the reaction was stopped with saturated ammonium chloride water. After fractionating the organic layer, the aqueous layer was extracted 4 times with dichloromethane. After combining the organic layers, they were dried with anhydrous sodium sulfate. After filtering the solution, it was vacuum concentrated, and the obtained mixture was fractionated by thin layer silica gel chromatography to obtain the corresponding optically active ester and a part of the unreacted optically active carboxylic acid. Then 1 M hydrochloric acid was added to the water layer, and after adjusting the pH to 2, extraction was carried out 4 times with dichloromethane. After-treatment was carried out in the same way as above, and unreacted optically active carboxylic acid was further recovered, and added to the previously obtained optically active carboxylic acid. The results are shown in Table 2.

TABLE 2

| No. | $R^3{}_n$ | Time | Yield of 2a/% (2a/2c) | Yield of 2b/% | ee/% 2a/2b | s |
|---|---|---|---|---|---|---|
| 9 | 2-Me | 9 h | 48 (3.4/1) | 11 | 15/11 | 2 |
| 10 | 2-MeO | 9 d | 60 (6.3/1) | 9 | 16/17 | 2 |
| 11 | 2-(2'-$C_6H_4OH$) | 13 h | 17 (3.6/1) | 21 | 41/19 | 3 |
| 12 | 2,6-$Me_2$ | 12 h | 12 (0.6/1) | 5 | 45/9 | 3 |
| 13 | 2,6-$Ph_2$ | 15 h | 19 (0.8/1) | 36 | 58/8 | 4 |
| 14 | 2,6-(1-Nap)$_2$ | 8 h | 14 (1.2/1) | 31 | 77/15 | 9 |
| 15 | 2,6-(2-Nap)$_2$ | 3 h | 29 (0.7/1) | 43 | 64/23 | 6 |

As can be understood from Table 2, when using as a phenol derivative 2,6-di(1-naphthyl)phenol or 2,6-di(2-naphthyl)phenol (Entries 14 and 15), it is possible to obtain the optically active esters and optically active carboxylic acids with a higher enantiomeric excess ratios ee and reaction rate ratios than for the case of using other phenol derivatives (Entries 9 to 13).

Experimental Example 3

Production of Optically Active Ester and Optically Active Carboxylic Acid Using 1,1-di(1-naphthyl)methanol

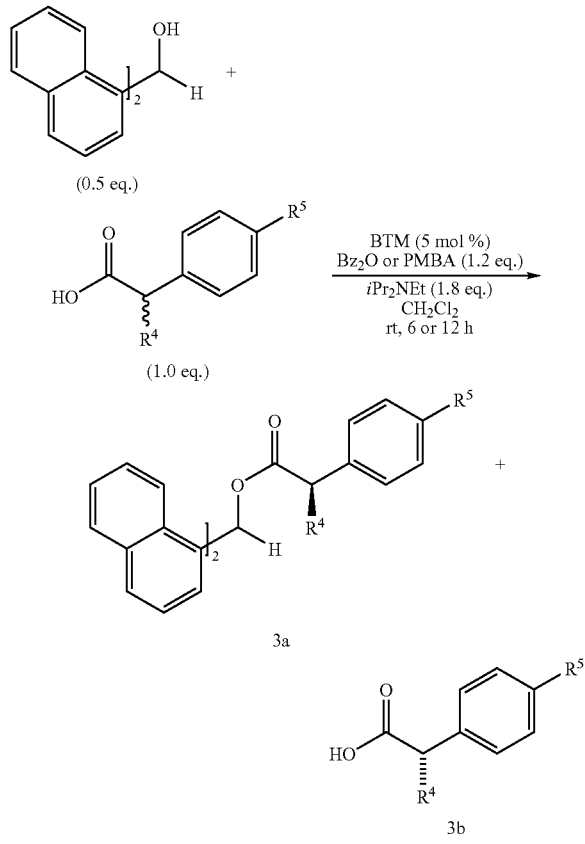

As shown in the above reaction equation, an optically active ester and optically active carboxylic acid were obtained by reacting 1,1-di(1-naphthyl)methanol and various racemic carboxylic acids. The results are shown in Table 3.

TABLE 3

| No. | $R^4$ | $R^5$ | Acid Anhydride | Time | Yield of 3a/% | Yield of 3b/% | ee/% 3a/3b | s |
|---|---|---|---|---|---|---|---|---|
| 16 | Me | H | PMBA | 12 h | 36 | 39 | 91/52 | 36 |
| 17 | Me | H | Bz$_2$O | 6 h | 45 | 29 | 89/48 | 27 |
| 18 | Me | Me | PMBA | 12 h | 37 | 31 | 83/45 | 17 |
| 19 | Me | Me | Bz$_2$O | 6 h | 30 | 23 | 85/28 | 16 |
| 20 | Me | OMe | PMBA | 12 h | 44 | 35 | 86/47 | 21 |
| 21 | Me | OMe | Bz$_2$O | 6 h | 49 | 29 | 84/65 | 22 |
| 22 | Me | Cl | PMBA | 12 h | 48 | 33 | 83/46 | 17 |
| 23 | Me | Cl | Bz$_2$O | 6 h | 52 | 26 | 83/27 | 14 |
| 24 | Et | H | PMBA | 12 h | 45 | 40 | 67/40 | 7.5 |
| 25 | Et | H | Bz$_2$O | 6 h | 46 | 29 | 39/30 | 3.0 |
| 26 | CH$_2$Ph | H | PMBA | 12 h | 55 | 37 | 58/41 | 5.5 |
| 27 | CH$_2$Ph | H | Bz$_2$O | 6 h | 48 | 28 | 73/43 | 10 |

As can be understood from Table 3, when using 1,1-di(1-naphthyl)methanol as the alcohol, optically active esters and optically active carboxylic acids were obtained with high enantiomer excess ratios ee and reaction rate ratios s, and high enantiomer selectivity rates.

Below, the production method and identification results of optically active esters and optically active carboxylic acids of Table 3 are shown.

Entry 16

To a dichloromethane solution (1.5 mL) containing p-methoxybenzoic anhydride (103.0 mg, 0.360 mmol) and racemic 2-phenylpropionic acid (45.1 mg, 0.300 mmol); diisopropylethylamine (94.0 µL, 0.540 mmol), benzotetramisole (3.8 mg, 0.015 mmol), and 1,1-di(1-naphthyl)methanol (42.8 mg, 0.151 mmol) were added in order at room temperature. After stirring the reaction mixture solution at room temperature for 12 hr, the reaction was stopped with saturated ammonium chloride water. After fractionating the organic layer, the aqueous layer was extracted 4 times with diethyl ether. After combining the organic layers, they were dried with anhydrous sodium sulfate. After filtering the solution, it was vacuum concentrated, and the obtained mixture was fractionated by thin layer silica gel chromatography to obtain the corresponding optically active ester (45.0 mg, 36%, 91% ee) and a part of the unreacted optically active carboxylic acid. Then 1 M hydrochloric acid was added to the water layer, and after adjusting the pH to 2, extraction was carried out 4 times with diethyl ether. After-treatment was carried out in the same way as above, and unreacted optically active carboxylic acid was further recovered, and added to the previously obtained optically active carboxylic acid (17.5 mg, 39%, 52% ee).

di-(1-naphthyl)methyl(R)-2-phenylpropanoate

HPLC (CHIRALPAK AD-H, i-PrOH/hexane=1/50, flow rate=1.0 mL/min): $t_R$=13.8 min (4.4%), $t_R$=18.3 min (95.6%);
Mp: 128° C. (i-PrOH/hexane);
IR (KBr): 3067, 1728, 1600, 1509, 776, 699 cm$^{-1}$;
$^1$H NMR (CDCl$_3$): δ8.29 (s, 1H, 1'-H), 7.99-7.94 (m, 1H, Ph), 7.84-7.79 (m, 1H, Ph), 7.74 (t, J=7.0 Hz, 2H, Ph), 7.68 (d, J=8.0 Hz, 1H, Ph), 7.63 (d, J=8.5 Hz, 1H, Ph), 7.45-7.38 (m, 2H, Ph), 7.35-7.31 (m, 1H, Ph), 7.23-7.14 (m, 7H, Ph), 7.11 (t, J=7.5 Hz, 1H, Ph), 7.06 (d, J=7.5 Hz, 1H, Ph), 6.90 (d, J=7.0 Hz, 1H, Ph), 3.77 (q, J=7.0 Hz, 1H, 2-H), 1.45 (d, J=7.0 Hz, 3H, 3-H);
$^{13}$C NMR (CDCl$_3$): δ173.5, 140.0, 134.8, 134.6, 133.8, 133.7, 131.2, 130.8, 129.1, 128.9, 128.7, 128.64, 128.57, 127.8, 127.2, 126.7, 126.4, 126.3, 125.9, 125.6, 125.2, 125.0, 123.5, 123.3, 71.1, 45.6, 18.2;
HR MS: calculated for C$_{30}$H$_{24}$O$_2$Na (M+Na$^+$)=439.1669. found 439.1668.

(S)-2-phenylpropionic acid

HPLC (CHIRALPAK AD-H, i-PrOH/hexane/TFA=1/50/0.05 flow rate=0.5 mL/min): $t_R$=39.6 min (24.1%), $t_R$=43.4 min (75.9%);
$^1$H NMR (CDCl$_3$): δ10.95 (br s, 1H, COOH), 7.30-7.16 (m, 5H, Ph), 3.67 (q, J=7.2 Hz, 1H, 2-H), 1.45 (d, J=7.2 Hz, 3H, 3-H).

Entry 18 di-(1-naphthyl)methyl(R)-2-(4-tolyl)propanoate

HPLC (CHIRALPAK AD-H, i-PrOH/hexane=1/9, flow rate=0.75 mL/min): $t_R$=9.5 min (7.6%), $t_R$=13.4 min (92.4%);

IR (neat): 3051, 1733, 1598, 1512, 801, 777, 732 cm$^{-1}$;

$^1$H NMR (CDCl$_3$): δ8.27 (s, 1H, 1'-H), 7.98-7.91 (m, 1H, Ph), 7.83-7.76 (m, 1H, Ph), 7.72 (t, J=8.2 Hz, 2H, Ph), 7.66 (d, J=8.2 Hz, 1H, Ph), 7.62 (d, J=8.6 Hz, 1H, Ph), 7.44-7.36 (m, 1H, Ph), 7.31 (t, J=7.5 Hz, 1H, Ph), 7.22-7.14 (m, 2H, Ph), 7.13-7.01 (m, 4H, Ph), 6.97 (d, J=7.9 Hz, 2H, Ph), 6.92 (d, J=7.5 Hz, 1H, Ph), 3.72 (q, J=7.0, 1H, 2-H), 2.25 (s, 3H, Me), 1.42 (d, J=7.0, 3H, 3-H);

$^{13}$C NMR (CDCl$_3$): δ173.7, 137.0, 136.7, 134.9, 134.6, 133.8, 133.7, 131.2, 130.9, 129.2, 129.1, 128.8, 128.7, 128.6, 128.3, 127.6, 126.7, 126.3, 126.2, 125.8, 125.6, 125.3, 125.2, 125.0, 123.5, 123.3, 71.1, 45.2, 21.0, 18.2;

HR MS: calculated for C$_{31}$H$_{26}$O$_2$ (M+Na$^+$)=453.1825. found 453.1816.

(S)-2-(4-tolyl)propionic acid

HPLC (CHIRALPAK AD-H, i-PrOH/hexane/TFA=1/50/0.05, flow rate=0.5 mL/min); t$_R$=43.2 min (23.0%), t$_R$=46.7 min (77.0%);

$^1$H NMR (CDCl$_3$): δ10.63 (br s, 1H, COOH), 7.13 (d, J=7.8, 2H, Ph), 7.07 (d, J=7.8, 2H, Ph), 3.63 (q, J=7.0 Hz, 1H, 2-H), 2.26 (s, 3H, Me), 1.42 (d, J=7.0 Hz, 3H, 3-H).

Entry 20 di(1-naphthyl)methyl(R)-2-(4-methoxyphenyl)propanoate

HPLC (CHIRALPAK AD-H, i-PrOH/hexane=1/9, flow rate=1.0 mL/min); t$_R$=10.5 min (7.2%), t$_R$=12.8 min (85.6%);

IR (neat): 3059, 1733, 1608, 1512, 783, 733 cm$^{-1}$;

$^1$H NMR (CDCl$_3$): δ8.26 (s, 1H, 1'-H), 7.97-7.89 (m, 1H, Ph), 7.85-7.58 (m, 5H, Ph), 7.46-7.04 (m, 8H, Ph), 6.93 (d, J=6.9 Hz, 1H, Ph), 6.75-6.67 (m, 2H, Ph), 3.78-3.68 (m, 4H, 2-H, OMe), 1.42 (d, J=6.9 Hz, 3H, 3-H);

$^{13}$C NMR (CDCl$_3$): δ173.7, 158.7, 134.8, 134.6, 133.8, 133.6, 132.1, 131.2, 130.9, 129.1, 128.83, 128.76, 128.7, 128.6, 128.3, 126.7, 126.3, 126.2, 125.8, 125.6, 125.3, 125.2, 125.0, 123.5, 123.3, 113.9, 71.0, 55.3, 44.8, 18.2;

HR MS: calculated for C$_{31}$H$_{26}$O$_2$Na (M+Na$^+$)=469.1774. found 469.1754.

(S)-2-(4-methoxyphenyl)propionic acid

HPLC (CHIRALPAK AD-H, i-PrOH/hexane/TFA=1/50/0.05, flow rate=1.0 mL/min); t$_R$=34.7 min (17.5%), t$_R$=36.4 min (82.5%);

$^1$H NMR (CDCl$_3$): δ10.99 (br s, 1H, COOH), 7.17 (d, J=8.7 Hz, 2H, Ph), 6.79 (d, J=8.7 Hz, 2H, Ph), 3.72 (s, 3H, OMe), 3.61 (q, J=7.2 Hz, 1H, 2-H), 1.42 (d, J=7.2 Hz, 3H, 3-H).

Entry 22 di(1-naphthyl)methyl(R)-2-(4-chlorophenyl)propanoate

HPLC (CHIRALPAK AD-H, i-PrOH/hexane=1/9, flow rate=0.5 mL/min); t$_R$=17.1 min (8.4%), t$_R$=19.3 min (91.6%);

IR (neat): 3052, 1737, 1599, 1510, 837, 777 cm$^{-1}$;

$^1$H NMR (CDCl$_3$): δ8.26 (d, J=3.0 Hz, 1H, 1'-H), 7.90 (dd, J=7.5, 3.0 Hz, 1H, Ph), 7.81 (d, J=7.5 Hz, 1H, Ph), 7.75 (t, J=8.5 Hz, 2H, Ph), 7.70 (d, J=8.0 Hz, 1H, Ph), 7.62 (dd, J=8.5, 3.0 Hz, 1H, Ph), 7.45-7.32 (m, 3H, Ph), 7.26-7.04 (m, 8H, Ph), 6.93 (dd, J=7.0, 3.0 Hz, 1H, Ph), 3.73 (qd, J=8.5, 1.5 Hz, 1H, 2-H), 1.45-1.41 (m, 3H, 3-H);

$^{13}$C NMR (CDCl$_3$): δ173.1, 138.4, 134.5, 134.4, 133.8, 133.7, 133.0, 131.1, 130.8, 129.2, 129.1, 128.9, 128.7, 128.6, 128.3, 126.7, 126.4, 126.1, 125.9, 125.7, 125.3, 125.2, 124.5, 123.3, 123.2, 71.4, 45.0, 18.0;

HR MS: calculated for C$_{30}$H$_{23}$O$_2$ClNa (M+Na$^+$)=473.1279. found 473.1284.

(S)-2-(4-chlorophenyl)propionic acid

HPLC (CHIRALPAK AD-H, i-PrOH/hexane/TFA=1/50/0.05, flow rate=0.75 mL/min); t$_R$=31.7 min (21.4%), t$_R$=34.0 min (78.6%);

$^1$H NMR (CDCl$_3$): δ9.15 (br s, 1H, COOH), 7.39-7.09 (m, 4H, Ph), 3.69 (q, J=7.0 Hz, 1H, 2-H), 1.48 (d, J=7.0 Hz, 3H, 3-H).

Entry 24 di(1-naphthyl)methyl(R)-2-phenylbutanoate

HPLC of 2-phenylbutan-1-ol derived from the title compound (CHIRALPAK AS-H, i-PrOH/hexane=1/50, flow rate=0.75 mL/min); t$_R$=16.0 min (16.4%), t$_R$=17.4 min (83.6%;

IR (neat): 3034, 1734, 1599, 1510, 779, 679 cm$^{-1}$;

$^1$H NMR (CDCl$_3$): δ8.28 (s, 1H, 1'-H), 7.94 (d, J=7.6 Hz, 1H, Ph), 7.82-7.76 (m, 1H, Ph), 7.71 (dd, J=8.3, 3.5 Hz, 2H, Ph), 7.64 (d, J=8.3 Hz, 1H, Ph), 7.59 (d, J=8.3 Hz, 1H, Ph), 7.43-7.34 (m, 2H, Ph), 7.33-7.26 (m, 1H, Ph), 7.20-7.11 (m, 7H, Ph), 7.10-7.02 (m, 2H, Ph), 6.88 (d, J=6.5, 1H, Ph), 3.50 (t, J=7.5 Hz, 1H, 2-H), 2.13-2.02 (m, 1H, 3-H), 1.78-1.67 (m, 1H, 3-H), 0.79 (t, J=7.3 Hz, 3H, 4-H);

$^{13}$C NMR (CDCl$_3$): δ173.0, 138.5, 134.8, 134.5, 133.8, 133.6, 131.2, 130.8, 129.1, 128.8, 128.7, 128.6, 128.5, 128.3, 128.2, 127.2, 126.7, 126.3, 126.2, 125.8, 125.6, 125.2, 125.0, 133.5, 123.3, 71.0, 53.5, 26.1, 12.2;

HR MS: calculated for C$_{31}$H$_{26}$O$_2$Na (M+Na$^+$)=453.1825. found 453.1834.

(S)-2-phenylbutanoic acid

HPLC (CHIRALPAK AD-H, i-PrOH/hexane/TFA=1/50/0.05, flow rate=1.0 mL/min); t$_R$=20.0 min (30.0%), t$_R$=22.8 min (70.0%);

$^1$H NMR (CDCl$_3$): δ10.28 (br s, 1H, COOH), 7.31-7.14 (m, 5H, Ph), 3.39 (t, J=7.5 Hz, 1H, 2-H), 2.13-1.93 (m, 1H, 3-H), 1.82-1.62 (m, 1H, 3-H), 0.83 (t, J=7.5 Hz, 3H, 4-H).

Entry 26 di(1-naphthyl)methyl(R)-2,3-diphenylpropanoate

HPLC (CHIRALPAK AD-H, i-PrOH/hexane=1/9, flow rate=0.75 mL/min); t$_R$=12.3 min (13.5%), t$_R$=23.1 min (86.5%);

IR (neat): 3033, 1736, 1600, 1511, 780, 678 cm$^{-1}$;

$^1$H NMR (CDCl$_3$): δ8.15 (s, 1H, 1'-H), 7.78-7.56 (m, 5H, Ph), 7.49 (t, J=8.3 Hz, 1H, Ph), 7.38-7.14 (m, 11H, Ph), 7.13-6.94 (m, 5H, Ph), 6.76 (dd, J=7.5 Hz, 1H, Ph), 7.06 (d, J=10.5, 7.0 Hz, 1H, Ph), 3.94 (dd, J=10.0, 5.5 Hz, 1H, 2-H), 3.40 (dd, J=13.7, 10.0 Hz, 1H, 3-H), 2.92 (dd, J=13.7, 5.5 Hz, 1H, 3-H);

$^{13}$C NMR (CDCl$_3$): δ172.4, 139.0, 138.2, 134.35, 134.30, 133.7, 133.6, 131.0, 130.8, 129.0, 128.9, 128.68, 128.63, 128.57, 128.4, 128.3, 128.1, 127.5, 126.7, 126.33, 126.31, 126.0, 125.7, 125.6, 125.20, 124.97, 123.4, 123.3, 71.4, 53.6, 39.2;

HR MS: calculated for $C_{36}H_{28}O_2Na$ (M+Na$^+$)=515.1982. found 515.1963.

(S)-2,3-diphenylpropionic acid

HPLC (CHIRALPAK AD-H, i-PrOH/hexane/TFA=1/10/0.01, flow rate=0.75 mL/min); $t_R$=12.5 min (21.9%), $t_R$=15.5 min (78.1%);

$^1$H NMR (CDCl$_3$): δ10.35 (br s, 1H, COOH), 7.28-6.98 (m, 10H, Ph), 3.78 (dd, J=8.2, 7.0 Hz, 1H, 2-H), 3.33 (dd, J=13.8, 8.2 Hz, 1H, 3-H), 2.96 (dd, J=13.8, 7.0 Hz, 1H, 3-H).

Experimental Example 4

Production of Optically Active Ester and Optically Active Carboxylic Acid Using 1,1-di(9-phenanthryl)methanol

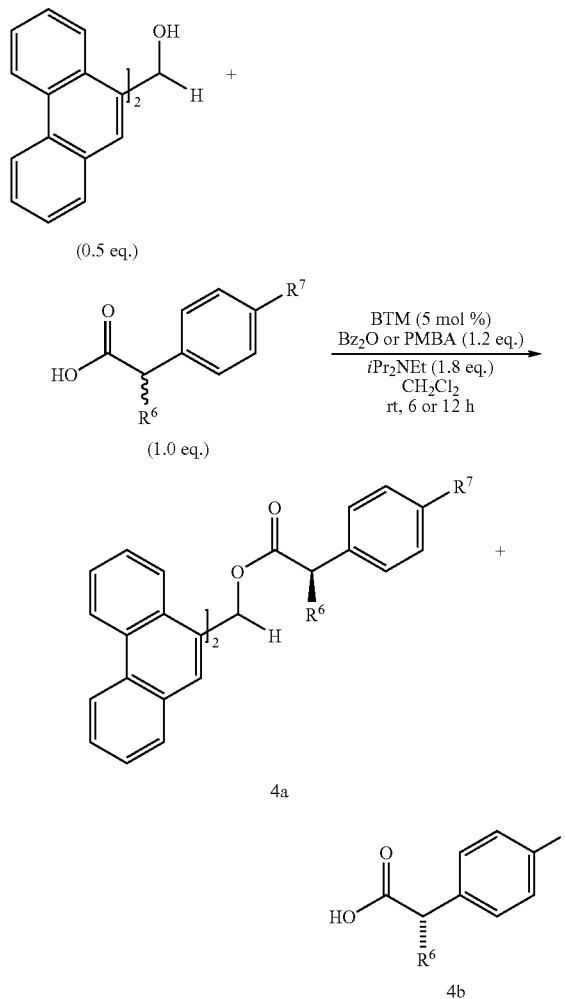

As shown in the above reaction equation, an optically active ester and optically active carboxylic acid are obtained by reacting 1,1-di(9-phenanthryl)methanol and various racemic carboxylic acids. The results are shown in Table 4.

TABLE 4

| No. | R$^6$ | R$^7$ | Acid Anhydride | Time | Yield of 4a/% | Yield of 4b/% | ee/% 4a/4b | s |
|---|---|---|---|---|---|---|---|---|
| 28 | Me | H | PMBA | 12 h | 42 | 42 | 91/52 | 37 |
| 29 | Me | H | Bz$_2$O | 6 h | 42 | 33 | 89/48 | 27 |
| 30 | Me | Me | PMBA | 12 h | 41 | 44 | 85/44 | 19 |
| 31 | Me | Me | Bz$_2$O | 6 h | 42 | 19 | 87/54 | 24 |
| 32 | Me | OMe | PMBA | 12 h | 39 | 42 | 82/49 | 16 |
| 33 | Me | OMe | Bz$_2$O | 6 h | 36 | 25 | 78/48 | 13 |
| 34 | Me | Cl | PMBA | 12 h | 47 | 43 | 80/57 | 16 |
| 35 | Me | Cl | Bz$_2$O | 6 h | 53 | 24 | 80/54 | 15 |
| 36 | Et | H | PMBA | 12 h | 25 | 63 | 76/16 | 8.5 |
| 37 | Et | H | Bz$_2$O | 6 h | 28 | 27 | 87/15 | 17 |
| 38 | CH$_2$Ph | H | PMBA | 12 h | 40 | 52 | 86/42 | 21 |
| 39 | CH$_2$Ph | H | Bz$_2$O | 6 h | 47 | 30 | 87/56 | 25 |

As can be understood from Table 4, when 1,1-di(9-phenanthryl)methanol is used as the alcohol, the enantiomer excess ratios ee and the reaction rate ratios s become high, and optically active esters and optically active carboxylic acids are obtained with a high enantiomer selectivity rate.

Below, the production method and identification results of optically active esters and optically active carboxylic acids in Table 4 are shown.

Entry 28

To a dichloromethane solution (2.0 mL) containing p-methoxybenzoic anhydride (68.7 mg, 0.240 mmol) and racemic 2-phenylpropionic acid (30.0 mg, 0.200 mmol); diisopropylethylamine (62.7 μL, 0.360 mmol), benzotetramisole (2.5 mg, 0.010 mmol), and 1,1-di(9-phenanthryl)methanol (38.4 mg, 0.100 mmol) were added in order at room temperature. After stirring the reaction mixture solution at room temperature for 12 hr, the reaction was stopped with saturated ammonium chloride water. After fractionating the organic layer, the aqueous layer was extracted 4 times with dichloromethane. After mixing the organic layers, they were dried with anhydrous sodium sulfate. After filtering the solution, it was vacuum concentrated, and the obtained mixture was fractionated by thin layer silica gel chromatography to obtain the corresponding optically active ester (43.3 mg, 42%, 91% ee) and a part of the unreacted optically active carboxylic acid. Then 1 M hydrochloric acid was added to the water layer, and after adjusting the pH to 2, extraction was carried out 4 times with dichloromethane. After-treatment was carried out in the same way as above, and unreacted optically active carboxylic acid was further recovered, and added to the previously obtained optically active carboxylic acid (12.4 mg, 42%, 52% ee).

di-(9-phenanthryl)methyl(R)-2-phenylpropanoate

HPLC (CHIRALPAK AD-H, i-PrOH/hexane=1/50, flow rate=0.5 mL/ml): $t_R$=30.0 min (95.6%), $t_R$=34.2 min (4.4%); IR (KBr): 3064, 1731, 1495, 1451, 1163, 749, 726 cm$^{-1}$;

$^1$H NMR (CDCl$_3$): δ8.82-8.59 (m, 4H, Ph), 8.42 (s, 1H, 1'-H), 8.20-8.11 (m, 1H, Ph), 7.84-7.25 (m, 18H, Ph), 3.91 (q, J=7.2 Hz, 1H, 2-H), 1.56 (d, J=7.2 Hz, 3H, 3-H);

$^{13}$C NMR (CDCl$_3$): δ173.5, 140.1, 132.9, 132.7, 131.1, 130.9, 130.7, 130.6, 130.5, 130.2, 129.8, 129.1, 128.8, 127.9, 127.4, 127.3, 127.2, 127.0, 126.9, 126.7, 126.5, 126.4, 126.2, 124.2, 123.9, 123.4, 123.1, 122.4, 122.4, 71.0, 45.7, 18.1.

Entry 30 di-(9-phenanthryl)methyl(R)-2-(4-tolyl)propanoate

HPLC (CHIRALPAK AD-H, i-PrOH/hexane=1/9, flow rate=0.5 mL/ml): $t_R$=26.7 min (93.3%), $t_R$=40.4 min (6.7%);

IR (KBr): 3068, 1732, 1451, 1154, 750, 726 cm$^{-1}$;
$^1$H NMR (CDCl$_3$): δ8.81-8.53 (m, 4H, Ph), 8.42 (s, 1H, 1'-H), 8.25-8.10 (m, 1H, Ph), 7.83-7.05 (m, 17H, Ph), 3.85 (q, J=6.9 Hz, 1H, 2-H), 2.40 (s, 3H, Me), 1.53 (d, J=6.9 Hz, 3H, 3-H);
$^{13}$C NMR (CDCl$_3$): δ173.6, 137.2, 137.0, 132.9, 132.7, 131.1, 131.1, 130.9, 130.7, 130.5, 130.2, 129.8, 129.5, 129.1, 129.1, 128.3, 128.0, 127.8, 127.3, 127.2, 127.0, 126.9, 126.6, 126.4, 126.4, 126.2, 124.3, 124.0, 123.4, 123.1, 122.4, 122.4, 70.8, 45.3, 21.1, 18.0.

Entry 32 di(9-phenanthryl)methyl(R)-2-(4-methoxyphenyl)propanoate

HPLC (CHIRALPAK AD-H, i-PrOH/hexane=1/50, flow rate=1.0 mL/ml): $t_R$=22.6 min (9.0%), $t_R$=26.3 min (91.0%);
IR (KBr): 3075, 1733, 1511, 1451, 1248, 1032, 750, 726 cm$^{-1}$;
$^1$H NMR (CDCl$_3$): δ8.84-8.64 (m, 4H, Ph), 8.40 (s, 1H, 1'-H), 8.18-8.12 (m, 1H, Ph), 7.80-7.35 (m, 12H, Ph), 7.30-7.19 (m, 3H, Ph), 6.88-6.82 (m, 2H, Ph), 3.86 (q, J=7.2 Hz, 1H, 2-H), 3.84 (s, 3H, OMe), 1.54 (d, J=7.2 Hz, 3H, 3-H);
$^{13}$C NMR (CDCl$_3$): δ173.0, 158.9, 133.0, 132.8, 132.2, 131.1, 131.0, 130.7, 130.6, 130.5, 130.3, 129.9, 129.1, 129.1, 129.0, 127.9, 127.3, 127.2, 127.0, 126.9, 126.7, 126.5, 126.4, 126.3, 124.3, 124.0, 123.4, 123.1, 122.5, 122.4, 114.2, 70.9, 55.3, 44.9, 18.1.

Entry 34 di(9-phenanthryl)methyl(R)-2-(4-chlorophenyl)propanoate

HPLC (CHIRALPAK AD-H, i-PrOH/hexane=1/50, flow rate=0.5 mL/ml): $t_R$=37.4 min (10.1%), $t_R$=46.4 min (89.8%);
IR (KBr): 3067, 1735, 1493, 1451, 1151, 750, 726 cm$^{-1}$;
$^1$H NMR (CDCl$_3$): δ8.87-8.63 (m, 4H, Ph), 8.40 (s, 1H, 1'-H), 8.17-8.09 (m, 1H, Ph), 7.80-7.20 (m, 17H, Ph), 3.89 (q, J=7.2 Hz, 1H, 2-H), 1.55 (d, J=7.2 Hz, 3H, 3-H);
$^{13}$C NMR (CDCl$_3$): δ173.0, 138.5, 133.3, 132.6, 132.5, 131.0, 130.9, 130.9, 130.6, 130.6, 130.4, 130.1, 129.7, 129.2, 129.1, 129.0, 128.3, 127.9, 127.3, 127.1, 126.9, 126.7, 126.5, 126.2, 124.1, 123.8, 123.4, 123.2, 122.4, 122.4, 71.1, 45.1, 17.9.

Entry 36 di(9-phenanthryl)methyl(R)-2-phenylbutanoate

HPLC (CHIRALPAK AD-H, i-PrOH/hexane=1/50, flow rate=0.5 mL/ml): $t_R$=23.4 min (93.5%), $t_R$=29.6 min (6.5%);
IR (KBr): 3057, 1727, 1450, 1359, 1154, 755, 727 cm$^{-1}$;
$^1$H NMR (CDCl$_3$): δ8.84-8.53 (m, 4H, Ph), 8.32 (s, 1H, 1'-H), 8.11-7.98 (m, 1H, Ph), 7.76-7.14 (m, 18H, Ph), 3.60 (dd, J=7.7, 7.7 Hz, 1H, 2-H), 2.22-2.04 (m, 1H, 3-H), 1.84-1.63 (m, 1H, 3-H), 0.87 (t, J=7.2 Hz, 3H, 4-H).

Entry 38 di(9-phenanthryl)methyl(R)-2,3-diphenylpropanoate

HPLC of 2,3-diphenylpropan-1-ol derived from the title compound (CHIRALPAK AD-H, i-PrOH/hexane=1/9, flow rate=0.5 mL/ml): $t_R$=14.7 min (93.4%), $t_R$=18.7 min (6.6%);

IR (KBr): 3064, 1723, 1495, 1451, 1145, 748, 726 cm$^{-1}$;
$^1$H NMR (CDCl$_3$): δ8.79-8.55 (m, 4H, Ph), 8.29 (s, 1H, 1'-H), 7.90-7.80 (m, 1H, Ph), 7.71-7.10 (m, 23H, Ph), 4.10 (dd, J=10.0, 5.4 Hz, 1H, 2-H), 3.54 (dd, J=13.9, 10.0 Hz, 1H, 3-H), 3.02 (dd, J=13.9, 5.4 Hz, 1H, 3-H);
$^{13}$C NMR (CDCl$_3$): δ172.3, 139.1, 138.4, 132.6, 132.5, 131.0, 131.0, 130.8, 130.6, 130.6, 130.4, 130.1, 129.7, 129.2, 129.1, 129.0, 128.9, 128.4, 128.3, 128.3, 127.9, 127.6, 127.3, 127.2, 127.0, 126.9, 126.9, 126.6, 126.5, 126.4, 126.4, 126.1, 124.3, 123.9, 123.3, 123.1, 122.4, 122.3, 71.3, 53.7, 39.3.

Experimental Example 5

Production of Optically Active Ester and Optically Active Carboxylic Acid Using 2,6-di(1-naphthyl)phenol and 2,6-di(2-naphthyl)phenol

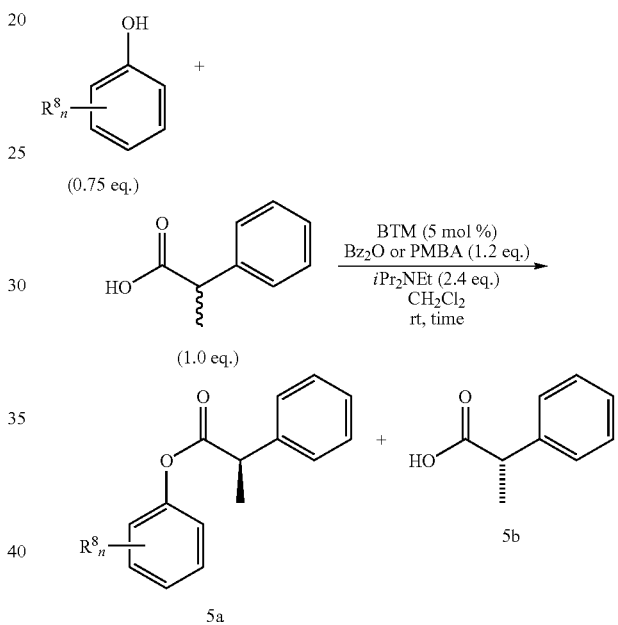

As shown by the above reaction equation, an optically active ester and optically active carboxylic acid are obtained by reacting 2,6-di(1-naphthyl)phenol and 2,6-di(2-naphthyl)phenol and racemic 2-phenolpropionic acid. The results are shown in Table 5.

TABLE 5

| No. | $R^8_n$ | Acid Anhydride | Time | Yield of 5a/% | Yield of 5b/% | ee/% 5a/5b | s |
|---|---|---|---|---|---|---|---|
| 40 | 2,6-(1-Nap)$_2$ | PMBA | 4 h | 21 | 58 | 86/18 | 16 |
| 41 | 2,6-(1-Nap)$_2$ | Bz$_2$O | 8 h | 14 | 31 | 77/15 | 9 |
| 42 | 2,6-(2-Nap)$_2$ | PMBA | 3 h | 15 | 71 | 67/11 | 6 |
| 43 | 2,6-(2-Nap)$_2$ | Bz$_2$O | 3 h | 29 | 43 | 64/23 | 6 |

As can be understood from Table 5, when 2,6-di(1-naphthyl)phenol and 2,6-di(2-naphthyl)phenol are used as a phenol derivative, in particular when 2,6-di(1-naphthyl)phenol is used as the phenol derivative and p-methoxybenzoic anhydride is used as the acid anhydride (Entry 40), the enantiomer excess ratios ee and the reaction rate ratios s become high, and an optically active ester and optically active carboxylic acid are obtained with a high enantiomer selectivity rate.

Below, the production method and identification results of optically active esters and optically active carboxylic acids in Table 5 are shown.

Entry 40

To a dichloromethane solution (1.5 mL) containing p-methoxybenzoic anhydride (103.1 mg, 0.360 mmol) and racemic 2-phenylpropionic acid (45.0 mg, 0.300 mmol); diisopropylethylamine (130.0 μL, 0.720 mmol), benzotetramisole (3.8 mg, 0.015 mmol), and 2,6-di(1-naphthyl)phenol (77.9 mg, 0.225 mmol) were added in order at room temperature. After stirring the reaction mixture solution at room temperature for 4 hr, the reaction was stopped with saturated ammonium chloride water. After fractionating the organic layer, the aqueous layer was extracted 4 times with dichloromethane. After combining the organic layers, they were dried with anhydrous sodium sulfate. After filtering the solution, it was vacuum concentrated, and the obtained mixture was fractionated by thin layer silica gel chromatography to obtain the corresponding optically active ester (29.8 mg, 21%, 86% ee) and a part of the unreacted optically active carboxylic acid. Then 1 M hydrochloric acid was added to the water layer, and after adjusting the pH to about 2, extraction was carried out 4 times with dichloromethane. After-treatment was carried out in the same way as above, and unreacted optically active carboxylic acid was further recovered, and added to the previously obtained optically active carboxylic acid (26.2 mg, 58%, 18% ee).

2,6-di(1-naphthyl)phenyl(R)-2-phenylpropanoate

HPLC (CHIRALPAK AD-H, i-PrOH/hexane=1/50, flow rate=0.3 mL/min); $t_R$=29.6 min (93.0%), $t_R$=33.6 min (7.0%);
$^1$H NMR (CDCl$_3$): δ7.92-7.65 (m, 6H, Ph), 7.55-7.29 (m, 1H, Ph), 7.02-6.69 (m, 3H, Ph), 6.27-6.10 (m, 2H, Ph), 2.75 (qd, J=7.2, 6.9 Hz, 1H, 2-H), 0.39 (dq, J=8.7, 7.2 Hz, 3H, 3-H).

Entry 42

To a dichloromethane solution (1.5 mL) containing p-methoxybenzoic anhydride (103.1 mg, 0.360 mmol) and racemic 2-phenylpropionic acid (45.0 mg, 0.300 mmol); diisopropylethylamine (130.0 μL, 0.720 mmol), benzotetramisole (3.8 mg, 0.015 mmol), and 2,6-di(2-naphthyl)phenol (77.9 mg, 0.225 mmol) were added in order at room temperature. After stirring the reaction mixture solution at room temperature for 3 hr, the reaction was stopped with saturated ammonium chloride water. After fractionating the organic layer, the aqueous layer was extracted 4 times with dichloromethane. After combining the organic layers, they were dried with anhydrous sodium sulfate. After filtering the solution, it was vacuum concentrated, and the obtained mixture was fractionated by thin layer silica gel chromatography to obtain the corresponding optically active ester 21.7 mg, 15%, 67% ee) and a part of the unreacted optically active carboxylic acid. Then 1 M hydrochloric acid was added to the water layer, and after adjusting the pH to about 2, extraction was carried out 4 times with dichloromethane. After-treatment was carried out in the same way as above, and unreacted optically active carboxylic acid was further recovered, and added to the previously obtained optically active carboxylic acid (31.5 mg, 71%, 11% ee).

2,6-di(2-naphthyl)phenyl(R)-2-phenylpropanoate

HPLC (CHIRALPAK AD-H, i-PrOH/hexane=1/50, flow rate=1.0 mL/min); $t_R$=21.3 min (16.3%), $t_R$=23.9 min (83.7%);
$^1$H NMR (CDCl$_3$): δ7.93-7.65 (m, 8H, Ph), 7.56-7.39 (m, 8H, Ph), 7.25 (s, 1H, Ph), 6.95-6.85 (m, 1H, Ph), 6.79-6.70 (m, 2H, Ph), 6.67-6.58 (m, 2H, Ph), 3.35 (q, J=7.2 Hz, 1H, 2-H), 0.95 (d, J=7.2 Hz, 3H, 3-H).

Experimental Example 6

Production of Optically Active Ester and Optically Active Carboxylic Acid Using Ibuprofen (Optical Resolution of Ibuprofen)

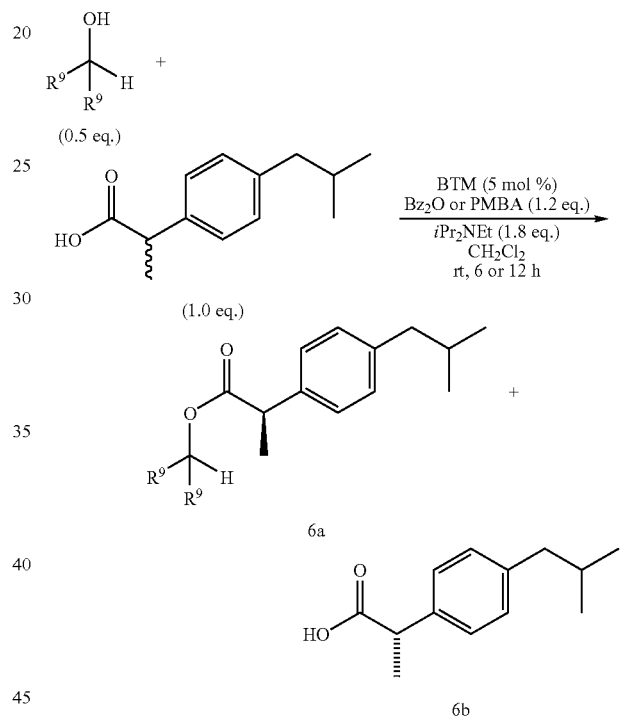

As shown by the above reaction equation, an optically active ester and optically active carboxylic acid are obtained by reacting 1,1-di(1-naphthyl)methanol or 1,1-di(9-phenanthryl)methanol and racemic ibuprofen. The results are shown in Table 6.

TABLE 6

| No. | $R^9$ | Acid Anhydride | Time | Yield of 6a/% | Yield of 6b/% | ee/% 6a/6b | s |
|---|---|---|---|---|---|---|---|
| 44 | 1-Nap | PMBA | 12 h | 39 | 33 | 92/36 | 34 |
| 45 | 1-Nap | Bz$_2$O | 6 h | 43 | 26 | 89/55 | 30 |
| 46 | 9-Phen | PMBA | 12 h | 39 | 30 | 89/49 | 27 |
| 47 | 9-Phen | Bz$_2$O | 6 h | 36 | 33 | 90/42 | 27 |

As can be understood from Table 6, both when using 1,1-di(1-naphthyl)methanol and when using 1,1-di(9-phenanthryl)methanol as the alcohol, ibuprofen is optically resolved with a high enantiomer selectivity, and an optically active ester and optically active carboxylic acid are obtained.

Below, the production method and identification results of optically active esters and optically active carboxylic acids in Table 6 are shown.

Entry 44

To a dichloromethane solution (1.0 mL) containing p-methoxybenzoic anhydride (68.9 mg, 0.241 mmol) and racemic ibuprofen (41.2 mg, 0.200 mmol); diisopropylethylamine (62.7 μL, 0.360 mmol), benzotetramisole (2.5 mg, 0.010 mmol), and 1,1-di(1-naphthyl)methanol (28.4 mg, 0.100 mmol) were added in order at room temperature. After stirring the reaction mixture solution at room temperature for 12 hr, the reaction was stopped with saturated ammonium chloride water. After fractionating the organic layer, the aqueous layer was extracted 4 times with diethylether. After combining the organic layers, they were dried with anhydrous sodium sulfate. After filtering the solution, it was vacuum concentrated, and the obtained mixture was fractionated by thin layer silica gel chromatography to obtain the corresponding optically active ibuprofen ester (36.9 mg, 39%, 92% ee) and the unreacted optically active ibuprofen (13.6 mg, 33%, 36% ee).

(R)-ibuprofen di(1-naphthyl)methylester

HPLC (CHIRALPAK AD-H, i-PrOH/hexane=1/9, flow rate=1.0 mL/ml); $t_R$=6.1 min (4.1%), $t_R$=10.7 min (95.9%);
IR (neat): 3036, 1735, 1599, 1512, 782, 679 cm$^{-1}$;
$^1$H NMR (CDCl$_3$): δ8.29 (s, 1H, 1"-H), 8.02-7.93 (m, 1H, Ph), 7.85-7.60 (m, 5H, Ph), 7.47-7.26 (m, 3H, Ph), 7.24-7.02 (m, 6H, Ph), 7.00-6.88 (m, 3H, Ph), 3.74 (q, J=7.1 Hz, 1H, 2-H), 2.38 (d, J=7.1 Hz, 2H, 1'-H), 1.78 (qq, J=6.6, 6.6 Hz, 1H, 2'-H), 1.43 (d, J=7.1 Hz, 3H, 3-H), 0.84 (d, J=6.6 Hz, 6H, 3'-H);
$^{13}$C NMR (CDCl$_3$): δ173.7, 140.6, 137.2, 134.9, 134.7, 133.8, 133.7, 131.2, 130.9, 129.3, 129.1, 128.8, 128.7, 128.6, 127.5, 126.7, 126.3, 125.8, 125.6, 125.2, 125.0, 123.5, 123.4, 70.9, 45.3, 45.0, 30.2, 22.4, 18.1;
HR MS: calculated for C$_{34}$H$_{32}$O$_2$Na (M+Na$^+$)=495.2295. found 495.2276.

(S)-ibuprofen

HPLC (CHIRALPAK AD-H, i-PrOH/hexane/TFA=1/100/0.1, flow rate=1.0 mL/min); $t_R$=26.3 min (77.5%), $t_R$=28.5 min (22.5%);
$^1$H NMR (CDCl$_3$): δ10.30 (br s, 1H, COOH), 7.14 (d, J=7.9 Hz, 2H, Ph), 7.02 (d, J=7.9 Hz, 2H, Ph), 3.63 (q, J=7.3 Hz, 1H, 2-H), 2.37 (q, J=7.3 Hz, 2H, 1'-H), 1.77 (qq, J=6.5, 6.5 Hz, 1H, 2'-H), 1.42 (d, J=7.3 Hz, 2H, 3-H), 0.82 (d, J=6.5 Hz, 6H, 3'-H).

Entry 46

(R)-ibuprofen di(9-phenanthryl)methylester

HPLC (CHIRALPAK AD-H, i-PrOH/hexane=1/50, flow rate=0.5 mL/ml); $t_R$=18.4 min (5.6%), $t_R$=24.9 min (94.4%);
IR (KBr): 3068, 1732, 1451, 1155, 750, 726 cm$^{-1}$;
$^1$H NMR (CDCl$_3$): δ8.83-8.60 (m, 4H, Ph), 8.40 (s, 1H, 1"-H), 8.18-8.09 (m, 1H, Ph), 7.82-7.04 (m, 17H, Ph), 3.89 (q, J=7.2 Hz, 1H, 2-H), 2.61-2.45 (m, 2H, 1'-H), 2.00-1.81 (m, 1H, 2'-H), 1.55 (d, J=7.2 Hz, 3H, 3-H), 0.95 (d, J=6.6 Hz, 6H, 3'-H);
$^{13}$C NMR (CDCl$_3$): δ173.7, 133.0, 132.7, 131.1, 131.0, 130.9, 130.6, 130.6, 130.4, 130.2, 129.8, 129.5, 129.1, 127.9, 127.5, 127.3, 127.2, 127.0, 126.9, 126.9, 126.6, 126.4, 126.2, 124.3, 123.9, 123.3, 123.1, 122.4, 122.4, 70.8, 45.3, 45.1, 30.2, 22.5, 22.4, 18.2.

Experimental Example 7

Production of Optically Active Ester and Optically Active Carboxylic Acid Using Ketoprofen (Optical Resolution of Ketoprofen)

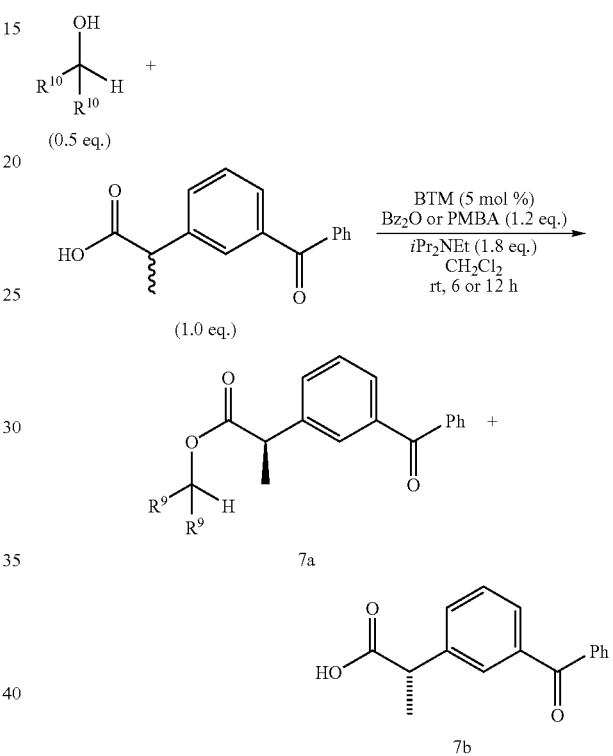

As shown by the above formula, an optically active ester and optically active carboxylic acid are obtained by reacting 1,1-di(1-naphthyl)methanol or 1,1-di(9-phenanthryl)methanol and racemic ketoprofen. The results are shown in Table 7.

TABLE 7

| No. | R$^{10}$ | Acid Anhydride | Time | Yield of 7a/% | Yield of 7b/% | ee/% 7a/7b | s |
|---|---|---|---|---|---|---|---|
| 48 | 1-Nap | PMBA | 12 h | 55 | 36 | 77/58 | 14 |
| 49 | 1-Nap | Bz$_2$O | 6 h | 55 | 27 | 80/50 | 15 |
| 50 | 9-Phen | PMBA | 12 h | 53 | 43 | 72/60 | 11 |
| 51 | 9-Phen | Bz$_2$O | 6 h | 49 | 19 | 75/43 | 11 |

As can be understood from Table 7, both when using 1,1-di(1-naphthyl)methanol and when using 1,1-di(9-phenanthryl)methanol as the alcohol, ketoprofen is optically resolved with a high enantiomer selectivity, and an optically active ester and optically active carboxylic acid are obtained.

Below, the production method and identification results of optically active esters and optically active carboxylic acids in Table 7 are shown.

Entry 49

To a dichloromethane solution (2.0 mL) containing benzoic anhydride (54.2 mg, 0.240 mmol) and racemic ketoprofen (50.8 mg, 0.200 mmol); diisopropylethylamine (62.7 μL, 0.360 mmol), benzotetramisole (2.5 mg, 0.010 mmol), and 1,1-di(1-naphthyl)methanol (28.4 mg, 0.100 mmol) were added in order at room temperature. After stirring the reaction mixture solution at room temperature for 6 hr, the reaction was stopped with saturated ammonium chloride water. After fractionating the organic layer, the aqueous layer was extracted 4 times with diethylether. After combining the organic layers, they were dried with anhydrous sodium sulfate. After filtering the solution, it was vacuum concentrated, and the obtained mixture was fractionated by thin layer silica gel chromatography to obtain the corresponding optically active ketoprofen ester (56.8 mg, 55%, 80% ee) and the unreacted optically active ketoprofen (13.8 mg, 27%, 50% ee).

(R)-ketoprofen di(1-naphthyl)methylester

HPLC (CHIRALPAK AD-H, i-PrOH/hexane=1/4, flow rate=1.0 mL/ml): $t_R$=16.7 min (10.1%), $t_R$=46.3 min (89.9%);

IR (neat): 3035, 1735, 1660, 1599, 1511, 780, 680 cm$^{-1}$;

$^1$H NMR (CDCl$_3$): δ8.28 (s, 1H, 1'-H), 7.93-7.85 (m, 1H, Ph), 7.82-7.54 (m, 6H, Ph), 7.52-7.44 (m, 2H, Ph), 7.44-7.06 (m, 13H, Ph), 6.95 (d, J=7.1 Hz, 1H, Ph), 3.81 (q, J=7.1 Hz, 1H, 2-H), 1.46 (d, J=7.1 Hz, 3H, 3-H);

$^{13}$C NMR (CDCl$_3$): δ196.3, 173.0, 140.1, 137.8, 137.3, 134.5, 134.4, 133.8, 133.7, 132.4, 131.6, 131.1, 130.8, 129.9, 129.5, 129.2, 128.93, 128.91, 128.86, 128.7, 128.6, 128.3, 128.2, 126.7, 126.4, 126.1, 125.9, 125.7, 125.4, 125.2, 125.0, 123.2, 71.4, 45.5, 17.9.

HR MS: calculated for C$_{37}$H$_{28}$O$_3$Na (M+Na$^+$)=543.1931. found 543.1910.

(S)-ketoprofen

HPLC (CHIRALPAK AD-H, i-PrOH/hexane/TFA=1/10/0.01, flow rate=1.0 mL/min); $t_R$=15.0 min (20.0%), $t_R$=17.7 min (80%);

$^1$H NMR (CDCl$_3$): δ10.67 (br s, 1H, COOH), 7.85-7.76 (m, 3H, Ph), 7.69 (dt, J=7.5, 1.5 Hz, 1H, Ph), 7.63-7.54 (m, 2H, Ph), 7.52-7.42 (m, 3H, Ph), 3.83 (q, J=7.0 Hz, 1H, 2-H), 1.56 (d, J=7.0 Hz, 3H, 3-H).

Entry 51

(R)-ketoprofen di(9-phenanthryl)methylester

HPLC (CHIRALPAK AD-H, i-PrOH/hexane=1/9, flow rate=1.0 mL/ml): $t_R$=34.6 min (86.0%), $t_R$=45.7 min (14.0%);

IR (neat): 3060, 1733, 1658, 1159, 754, 721 cm$^{-1}$;

$^1$H NMR (CDCl$_3$): δ8.84-8.60 (m, 4H, Ph), 8.42 (s, 1H, 1'-H), 8.16-8.06 (m, 1H, Ph), 7.82-7.32 (m, 20H, Ph), 7.28-7.32 (m, 2H, Ph), 3.99 (q, J=6.9 Hz, 1H, 2-H), 1.60 (d, J=6.9 Hz, 3H, 3-H);

$^{13}$C NMR (CDCl$_3$): δ196.3, 173.1, 140.2, 138.0, 137.4, 134.6, 134.5, 133.9, 133.7, 132.4, 131.6, 131.2, 131.0, 130.0, 129.6, 129.2, 128.9, 128.7, 128.6, 128.3, 128.2, 126.7, 126.5, 126.1, 125.9, 125.8, 125.4, 125.2, 125.0, 123.3, 71.5, 45.6, 18.0.

Experimental Example 8

Production of Optically Active Ester and Optically Active Carboxylic Acid Using Naproxen (Optical Resolution of Naproxen)

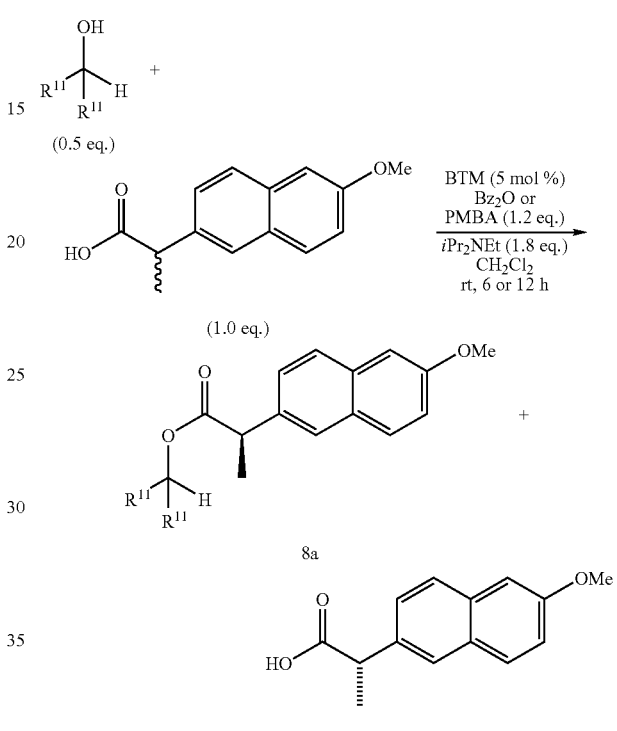

As shown by the above reaction equation, an optically active ester and optically active carboxylic acid are obtained by reacting 1,1-di(1-naphthyl)methanol or 1,1-di(9-phenanthryl)methanol and racemic naproxen. The results are shown in Table 8.

TABLE 8

| No. | R$^{11}$ | Acid Anhydride | Time | Yield of 8a/% | Yield of 8b/% | ee/% 8a/8b | s |
|---|---|---|---|---|---|---|---|
| 52 | 1-Nap | PMBA | 12 h | 53 | 37 | 77/62 | 15 |
| 53 | 1-Nap | Bz$_2$O | 6 h | 52 | 36 | 79/62 | 16 |
| 54 | 9-Phen | PMBA | 12 h | 49 | 42 | 87/61 | 26 |
| 55 | 9-Phen | Bz$_2$O | 6 h | 50 | 27 | 88/61 | 30 |

As can be understood from Table 8, both when using 1,1-di(1-naphthyl)methanol and when using 1,1-di(9-phenanthryl)methanol as the alcohol, naproxen is optically resolved with a high enantiomer selectivity, and an optically active ester and optically active carboxylic acid are obtained.

Below, the production method and identification results of optically active esters and optically active carboxylic acids in Table 8 are shown.

Entry 55

To a dichloromethane solution (2.0 mL) containing benzoic anhydride (54.3 mg, 0.240 mmol) and racemic naproxen (46.1 mg, 0.200 mmol); diisopropylethylamine (62.7 μL, 0.360 mmol), benzotetramisole (2.5 mg, 0.010 mmol), and 1,1-di(9-phenanthryl)methanol (38.4 mg, 0.100 mmol) were added in order at room temperature. After stirring the reaction mixture solution at room temperature for 6 hr, the reaction was stopped with saturated ammonium chloride water. After fractionating the organic layer, the aqueous layer was extracted 4 times with dichloromethane. After combining the organic layers, they were dried with anhydrous sodium sulfate. After filtering the solution, it was vacuum concentrated, and the obtained mixture was fractionated by thin layer silica gel chromatography to obtain the corresponding optically active naproxen ester (59.7 mg, 50%, 88% ee) and the unreacted optically active naproxen (12.6 mg, 27%, 61% ee).

(R)-naproxen di(9-phenanthryl)methylester

HPLC (CHIRALCELL OD-H, i-PrOH/hexane=1/4, flow rate=0.75 mL/mi): $t_R$=23.7 min (94.1%), $t_R$=41.1 min (5.9%);

IR (KBr): 3063, 1731, 1605, 1265, 1028, 749, 727 $cm^{-1}$;

$^1$H NMR (CDCl$_3$): δ8.84-8.50 (m, 4H, Ph), 8.43 (s, 1H, 1'-H), 8.25-8.12 (m, 1H, Ph), 7.80-7.08 (m, 18H, Ph), 6.83-6.75 (m, 1H, Ph), 4.03 (q, J=7.1 Hz, 1H, 2-H), 3.96 (s, 3H, OMe), 1.64 (d, J=7.1 Hz, 3H, 3-H);

$^{13}$C NMR (CDCl$_3$): δ173.5, 157.9, 135.2, 134.0, 132.9, 132.6, 131.0, 130.9, 130.6, 130.6, 130.3, 130.2, 129.8, 129.5, 129.1, 129.0, 128.9, 128.3, 128.0, 127.4, 127.3, 127.2, 126.8, 126.6, 126.6, 126.5, 126.4, 126.3, 126.2, 124.2, 123.9, 123.4, 123.1, 122.4, 122.2, 119.0, 105.6, 71.0, 55.4, 45.7, 18.0.

(S)-naproxen

HPLC (CHIRALPAK AD-H, i-PrOH/hexane/TFA=1/10/0.01, flow rate=1.0 mL/min); $t_R$=13.8 min (18.9%), $t_R$=15.8 min (81.1%);

$^1$H NMR (CDCl$_3$): δ9.42 (br s, 1H, COOH), 7.68-7.55 (m, 3H, Ph), 7.33-7.28 (m, 1H, Ph), 7.13-6.99 (m, 2H, Ph), 3.83 (s, 3H, OMe), 3.79 (q, J=7.2 Hz, 1H, 2-H), 1.50 (d, J=7.2 Hz, 3H, 3-H).

Entry 53

(R)-naproxen di(1-naphthyl)methylester

HPLC (CHIRALPAK AD-H, i-PrOH/hexane=1/9, flow rate=1.0 mL/ml): $t_R$=13.7 min (10.6%), $t_R$=17.4 min (89.4%);

IR (neat): 3034, 1733, 1604, 1508, 782, 679 $cm^{-1}$;

$^1$H NMR (CDCl$_3$): δ8.29 (s, 1H, 1'-H), 8.00-7.90 (m, 1H, Ph), 7.82-6.96 (m, 17H, Ph), 6.95-6.81 (m, 2H, Ph), 3.86 (q, J=7.0 Hz, 1H, 2-H), 3.79 (s, 3H, OMe), 1.49 (d, J=7.0 Hz, 3H, 3-H);

$^{13}$C NMR (CDCl$_3$): δ173.6, 157.6, 135.1, 134.7, 134.5, 133.8, 133.7, 133.6, 131.2, 130.8, 129.3, 129.1, 128.9, 128.8, 128.7, 128.6, 128.3, 127.1, 126.7, 126.5, 126.3, 126.2, 125.8, 125.6, 125.3, 125.2, 125.0, 123.4, 123.3, 118.9, 105.5, 71.2, 55.2, 45.5, 18.3;

HR MS: calculated for $C_{35}H_{28}O_3Na$ $(M+Na^+)$=519.1931. found 519.1932.

Experimental Example 9

Production of Optically Active Ester and Optically Active Carboxylic Acid Using Flurbiprofen (Optical Resolution of Flurbiprofen)

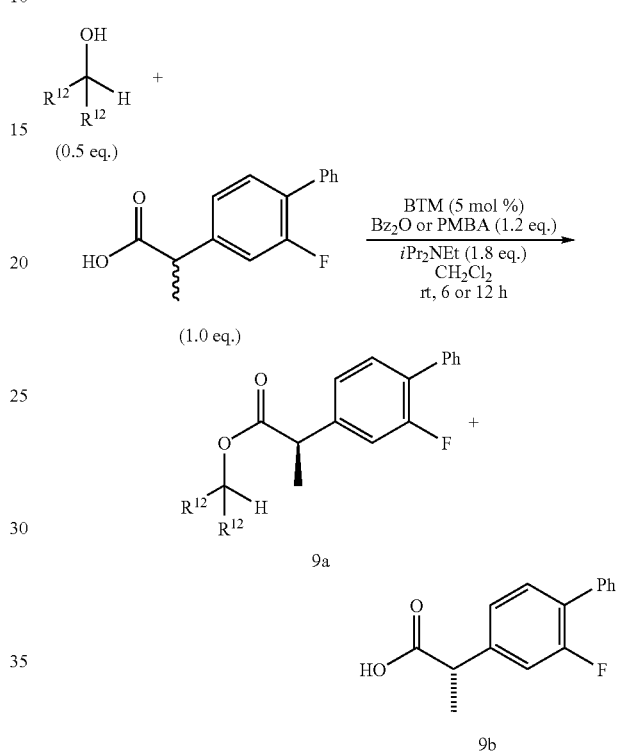

As shown by the above reaction equation, an optically active ester and optically active carboxylic acid are obtained by reacting 1,1-di(1-naphthyl)methanol or 1,1-di(9-phenanthryl)methanol and racemic flurbiprofen. The results are shown in Table 9.

TABLE 9

| No. | $R^{12}$ | Acid Anhydride | Time | Yield of 9a/% | Yield of 9b/% | ee/% 9a/9b | s |
|---|---|---|---|---|---|---|---|
| 56 | 1-Nap | PMBA | 12 h | 53 | 34 | 83/37 | 15 |
| 57 | 1-Nap | Bz$_2$O | 6 h | 53 | 25 | 83/8 | 12 |
| 58 | 9-Phen | PMBA | 12 h | 48 | 32 | 81/64 | 18 |
| 59 | 9-Phen | Bz$_2$O | 6 h | 41 | 28 | 88/44 | 23 |

As can be understood from Table 9, both when using 1,1-di(1-naphthyl)methanol and when using 1,1-di(9-phenanthryl)methanol as the alcohol, flurbiprofen is optically resolved with a high enantiomer selectivity, and an optically active ester and optically active carboxylic acid are obtained.

Below, the production method and identification results of optically active esters and optically active carboxylic acids in Table 9 are shown.

Entry 59

To a dichloromethane solution (2.0 mL) containing benzoic anhydride (54.3 mg, 0.240 mmol) and racemic flurbiprofen (48.9 mg, 0.200 mmol); diisopropylethylamine (62.7 µL, 0.360 mmol), benzotetramisole (2.5 mg, 0.010 mmol), and 1,1-di(9-phenanthryl)methanol (38.4 mg, 0.100 mmol) were added in order at room temperature. After stirring the reaction mixture solution at room temperature for 6 hr, the reaction was stopped with saturated ammonium chloride water. After fractionating the organic layer, the aqueous layer was extracted 4 times with dichloromethane. After combining the organic layers, they were dried with anhydrous sodium sulfate. After filtering the solution, it was vacuum concentrated, and the obtained mixture was fractionated by thin layer silica gel chromatography to obtain the corresponding optically active flurbiprofen ester (50.4 mg, 41%, 88% ee) and the unreacted optically active flurbiprofen (13.4 mg, 28%, 44% ee).

(R)-flurbiprofen di(9-phenanthryl)methylester

HPLC (CHIRALPAK AD-H, i-PrOH/hexane=1/9, flow rate=0.5 mL/ml): $t_R$=14.9 min (6.3%), $t_R$=16.9 min (93.7%);

IR (KBr): 3062, 1736, 1450, 1416, 1166, 1146, 749, 726 cm$^{-1}$;

$^1$H NMR (CDCl$_3$): δ8.84-8.62 (m, 4H, Ph), 8.42 (s, 1H, 1'-H), 8.17-8.08 (m, 1H, Ph), 7.80-7.32 (m, 19H, Ph), 7.20-7.11 (m, 2H, Ph), 3.95 (q, J=7.0 Hz, 1H, 2-H), 1.60 (d, J=7.0 Hz, 3H, 3-H);

$^{13}$C NMR (CDCl$_3$): δ172.9, 160.7, 158.8, 141.4, 141.3, 135.5, 132.7, 132.6, 131.0, 131.0, 130.9, 130.7, 130.6, 130.5, 130.1, 129.8, 129.1, 129.0, 129.0, 128.5, 128.1, 128.0, 127.9, 127.8, 127.3, 127.1, 127.0, 126.7, 126.7, 126.7, 126.5, 126.4, 124.2, 123.9, 123.9, 123.9, 123.4, 123.2, 122.5, 122.4, 115.7, 115.5, 71.3, 45.2, 17.8.

(S)-flurbiprofen

HPLC (CHIRALPAK AD-H, i-PrOH/hexane/TFA=1/50/0.05, flow rate=1.0 mL/min); $t_R$=24.9 min (18.2%), $t_R$=35.0 min (81.8%);

$^1$H NMR (CDCl$_3$): δ9.45 (br s, 1H, COOH), 7.57-7.49 (m, 2H, Ph), 7.48-7.33 (m, 4H, Ph), 7.22-7.11 (m, 2H, Ph), 3.80 (q, J=7.2 Hz, 1H, 2-H), 1.56 (d, J=7.2 Hz, 3H, 3-H).

Entry 57

(R)-flurbiprofen di(1-naphthyl)methylester

HPLC (CHIRALPAK AD-H, i-PrOH/hexane=1/9, flow rate=0.75 mL/ml): $t_R$=9.8 min (8.3%), $t_R$=16.9 min (91.7%);

IR (neat): 3035, 1734, 1599, 1513, 783, 679 cm$^{-1}$;

$^1$H NMR (CDCl$_3$): δ8.29 (s, 1H, 1'-H), 7.95-7.86 (m, 1H, Ph), 7.80-7.72 (m, 1H, Ph), 7.70 (d, J=8.1 Hz, 2H, Ph), 7.64 (d, J=8.1 Hz, 2H, Ph), 7.46-7.04 (m, 12H, Ph), 7.01-6.90 (m, 3H, Ph), 3.74 (q, J=7.0 Hz, 1H, 2-H), 1.44 (t, J=7.0 Hz, 3H, 3-H);

$^{13}$C NMR (CDCl$_3$): δ173.5, 140.0, 134.8, 134.6, 133.8, 133.7, 131.2, 130.8, 129.1, 128.9, 128.7, 128.64, 128.57, 127.8, 127.2, 126.7, 126.4, 126.3, 125.9, 125.6, 125.2, 125.0, 123.5, 123.3, 71.1, 45.6, 18.2;

HR MS: calculated for $C_{36}H_{27}O_2FNa$ (M+Na$^+$)=533.1887. found 533.1865.

Experimental Example 10

Production of Optically Active Ester and Optically Active Carboxylic Acid Using Fenoprofen (Optical Resolution of Fenoprofen)

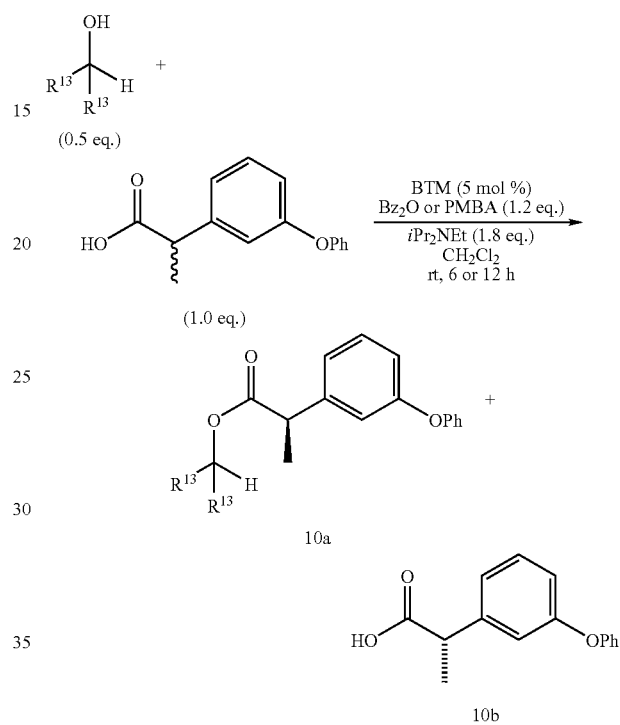

As shown by the above reaction equation, an optically active ester and optically active carboxylic acid are obtained by reacting 1,1-di(1-naphthyl)methanol or 1,1-di(9-phenanthryl)methanol and racemic fenoprofen. The results are shown in Table 10.

TABLE 10

| No. | R$^{13}$ | Acid Anhydride | Time | Yield of 10a/% | Yield of 10b/% | ee/% 10a/10b | s |
|---|---|---|---|---|---|---|---|
| 60 | 1-Nap | PMBA | 12 h | 46 | 42 | 82/53 | 17 |
| 61 | 1-Nap | Bz$_2$O | 6 h | 46 | 34 | 84/40 | 16 |
| 62 | 9-Phen | PMBA | 12 h | 47 | 39 | 78/60 | 15 |
| 63 | 9-Phen | Bz$_2$O | 6 h | 54 | 36 | 78/50 | 14 |

As can be understood from Table 10, both when using 1,1-di(1-naphthyl)methanol and when using 1,1-di(9-phenanthryl)methanol as the alcohol, fenoprofen is optically resolved with a high enantiomer selectivity, and an optically active ester and optically active carboxylic acid are obtained.

Below, the production method and identification results of optically active esters and optically active carboxylic acids in Table 10 are shown.

Entry 60

To a dichloromethane solution (1.0 mL) containing p-methoxybenzoic anhydride (68.7 mg, 0.240 mmol) and racemic fenoprofen (48.2 mg, 0.199 mmol), and 1,1-di(naphthyl)methanol (28.2 mg, 0.099 mmol); diisopropylethylamine (62.7 μL, 0.360 mmol) and benzotetramisole (2.5 mg, 0.010 mmol), were added in order at room temperature. After stirring the reaction mixture solution at room temperature for 12 hr, the reaction was stopped with saturated ammonium chloride water. After fractionating the organic layer, the aqueous layer was extracted 4 times with diethyl ether. After combining the organic layers, they were dried with anhydrous sodium sulfate. After filtering the solution, it was vacuum concentrated, and the obtained mixture was fractionated by thin layer silica gel chromatography to obtain the corresponding optically active fenoprofen ester (46.8 mg, 46%, 82% ee) and the unreacted optically active fenoprofen (20.2 mg, 42%, 53% ee).

(R)-fenoprofen di(1-naphthyl)methylester

HPLC (CHIRALPAK AD-H, i-PrOH/hexane=1/50, flow rate=1.0 mL/ml): $t_R$=20.4 min (8.9%), $t_R$=23.9 min (91.1%);
IR (neat): 3036, 1735, 1585, 1484, 781, 679 cm$^{-1}$;
$^1$H NMR (CDCl$_3$): δ8.28 (s, 1H, 1'-H), 7.92 (d, J=8.0 Hz, 1H, Ph), 7.82-7.62 (m, 5H, Ph), 7.43-7.30 (m, 3H, Ph), 7.27-7.09 (m, 7H, Ph), 6.98-6.91 (m, 3H, Ph), 6.86-6.83 (m, 1H, Ph), 6.82-6.73 (m, 3H, Ph), 3.72 (q, J=7.0 Hz, 1H, 2-H), 1.42 (d, J=7.0 Hz, 3H, 3-H);
$^{13}$C NMR (CDCl$_3$): δ173.1, 157.3, 157.0, 141.9, 134.7, 134.6, 133.8, 133.7, 131.2, 130.9, 129.8, 129.7, 129.1, 128.9, 128.8, 128.7, 128.3, 126.7, 126.4, 126.1, 125.9, 125.7, 125.3, 125.2, 125.1, 123.4, 123.3, 123.1, 122.6, 118.7, 118.4, 117.6, 71.2, 45.5, 17.9;
HR MS: calculated for C$_{36}$H$_{28}$O$_3$Na (M+Na$^+$)=531.1931. found 531.1948.

(S)-fenoprofen

HPLC (CHIRALPAK AD-H, i-PrOH/hexane/TFA=1/50/0.05, flow rate=1.0 mL/min); $t_R$=26.0 min (23.4%), $t_R$=30.9 min (76.6%);
$^1$H NMR (CDCl$_3$): δ11.8 (br s, 1H, COOH), 7.24-7.10 (m, 3H, Ph), 7.00-6.85 (m, 5H, Ph), 6.76 (ddd, J=8.2, 2.5, 0.9 Hz, 1H, Ph), 3.58 (q, J=7.2 Hz, 1H, 2-H), 1.37 (d, J=7.2 Hz, 3H, 3-H).

Entry 62

(R)-fenoprofen di(1-phenanthryl)methylester

HPLC (CHIRALPAK AD-H, i-PrOH/hexane=1/9, flow rate=0.5 mL/ml): $t_R$=17.9 min (88.9%), $t_R$=20.8 min (11.1%);
IR (KBr): 3070, 1736, 1584, 1486, 1232, 751, 726 cm$^{-1}$;
$^1$H NMR (CDCl$_3$): δ8.85-8.60 (m, 4H, Ph), 8.40 (s, 1H, 1'-H), 8.20-8.05 (m, 1H, Ph), 7.82-6.72 (m, 22H, Ph), 7.20-7.11 (m, 2H, Ph), 3.88 (q, J=7.2 Hz, 1H, 2-H), 1.55 (d, J=7.2 Hz, 3H, 3-H);
$^{13}$C NMR (CDCl$_3$): δ173.1, 157.6, 156.8, 142.0, 132.8, 132.7, 131.1, 131.1, 130.9, 130.7, 130.7, 130.5, 130.2, 130.0, 129.8, 129.6, 129.1, 129.1, 127.8, 127.3, 127.1, 127.0, 126.7, 126.7, 126.7, 126.6, 126.5, 126.5, 124.2, 124.0, 123.4, 123.3, 123.2, 122.6, 122.5, 122.4, 118.9, 118.3, 117.5, 71.2, 45.6, 17.9;
HR MS: calculated for C$_{44}$H$_{32}$O$_3$Na (M+Na$^+$)=631.2244. found 631.2254.

The invention claimed is:

1. A method for producing an optically active ester and an optically active carboxylic acid comprising:
reacting a racemic carboxylic acid with an alcohol shown by the formula (a) below, in the presence of a benzoic anhydride or its derivative and a catalyst shown by any of the formulae (e) and (f) below, and
selectively esterifying one enantiomer of the racemic carboxylic acid, wherein formula (a) has the structure

where R$^a$ represents a phenyl group, naphthyl group, anthryl group, or phenanthryl group, which may have a substituent group, formulae (e) and (f) have the respective structures

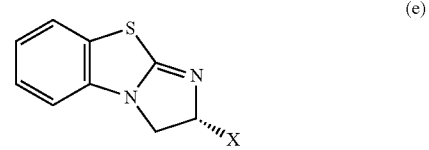

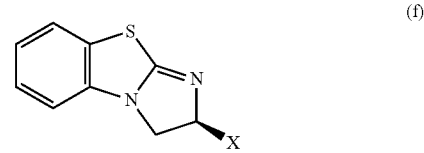

where X represents a phenyl group,
and the racemic carboxylic acid is shown by the formula (g) below

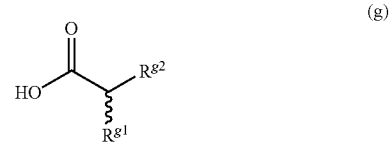

where R$^{g1}$ and R$^{g2}$ represent organic groups which differ from each other, R$^{g1}$ is an alkyl group, which may have a substituent group, and R$^{g2}$ is an aryl group, a heteroaryl group, an alkenyl group, or an alkynyl group, which may have a substituent group.

* * * * *

UNITED STATES PATENT AND TRADEMARK OFFICE
CERTIFICATE OF CORRECTION

PATENT NO. : 8,115,008 B2
APPLICATION NO. : 12/675326
DATED : February 14, 2012
INVENTOR(S) : Isamu Shiina and Kenya Nakata It is certified that error appears in the above-identified patent and that said Letters Patent is hereby corrected as shown below:

On the Title Page; item [73]:
The assignee reads – Tokyo University of Science Education Foundation Administrative Organization
The assignee should read – Tokyo University of Science Educational Foundation Administrative Organization Signed and Sealed this
Eighteenth Day of September, 2012

David J. Kappos
*Director of the United States Patent and Trademark Office*